(12) United States Patent
Cezar et al.

(10) Patent No.: US 11,197,944 B2
(45) Date of Patent: Dec. 14, 2021

(54) COMPOSITIONS AND METHODS OF MECHANICALLY INDUCING TISSUE REGENERATION

(71) Applicants: President and Fellows of Harvard College, Cambridge, MA (US); CHARITE—UNIVERSITAETSMEDIZIN BERLIN, Berlin (DE)

(72) Inventors: Christine A. Cezar, Cambridge, MA (US); Conor J. Walsh, Cambridge, MA (US); David J. Mooney, Sudbury, MA (US); Ellen T. Roche, Galway (IE); Herman H. Vandenburgh, Providence, RI (US); Georg N. Duda, Berlin (DE)

(73) Assignees: President and Fellows of Harvard College, Cambridge, MA (US); CHARITÉ UNIVERSITÄTSMEDIZIN BERLIN, Berlin (DE)

( * ) Notice: Subject to any disclaimer, the term of this patent is extended or adjusted under 35 U.S.C. 154(b) by 475 days.

(21) Appl. No.: 15/776,853

(22) PCT Filed: Nov. 18, 2016

(86) PCT No.: PCT/US2016/062685
§ 371 (c)(1),
(2) Date: May 17, 2018

(87) PCT Pub. No.: WO2017/087754
PCT Pub. Date: May 26, 2017

(65) Prior Publication Data
US 2020/0222582 A1    Jul. 16, 2020

Related U.S. Application Data

(60) Provisional application No. 62/305,323, filed on Mar. 8, 2016, provisional application No. 62/256,877, filed on Nov. 18, 2015.

(51) Int. Cl.
*A61L 27/04*   (2006.01)
*A61L 27/56*   (2006.01)
*A61L 27/14*   (2006.01)

(52) U.S. Cl.
CPC ............. *A61L 27/042* (2013.01); *A61L 27/14* (2013.01); *A61L 27/56* (2013.01); *A61L 2400/06* (2013.01); *A61L 2430/30* (2013.01)

(58) Field of Classification Search
CPC .... A61L 2430/30; A61L 27/50; A61L 27/042; A61L 27/54; A61L 27/56; A61L 2400/06;
(Continued)

(56) References Cited

U.S. PATENT DOCUMENTS

| 5,098,369 A | 3/1992 | Heilman et al. |
| 7,361,638 B2 | 4/2008 | Berlanga Acosta et al. |
| 7,497,837 B2 | 3/2009 | Sherman et al. |

FOREIGN PATENT DOCUMENTS

| WO | 2011/075516 A2 | 6/2011 | |
| WO | WO-2011075516 A2 * | 6/2011 | ........... A61K 9/0024 |

* cited by examiner

*Primary Examiner* — Jianfeng Song
(74) *Attorney, Agent, or Firm* — McCarter & English, LLP; Maria Laccotripe Zacharakis; Wei Song

(57) ABSTRACT

The present invention provides methods and compositions for promoting regeneration of a tissue, methods for preventing or reducing inflammation of a tissue, methods for preventing or reducing fibrosis of a tissue, methods for increasing a mass of a tissue, methods for increasing a level of oxygen available to a tissue, methods for increasing a rate of metabolic waste removal from a tissue, methods for increasing blood perfusion to a tissue, and methods of treating severe muscle tissue damage in a subject in need thereof by contacting the tissue with a composition that is suitable for applying cyclic mechanical compression to the tissue.

15 Claims, 13 Drawing Sheets

Figure 2B:
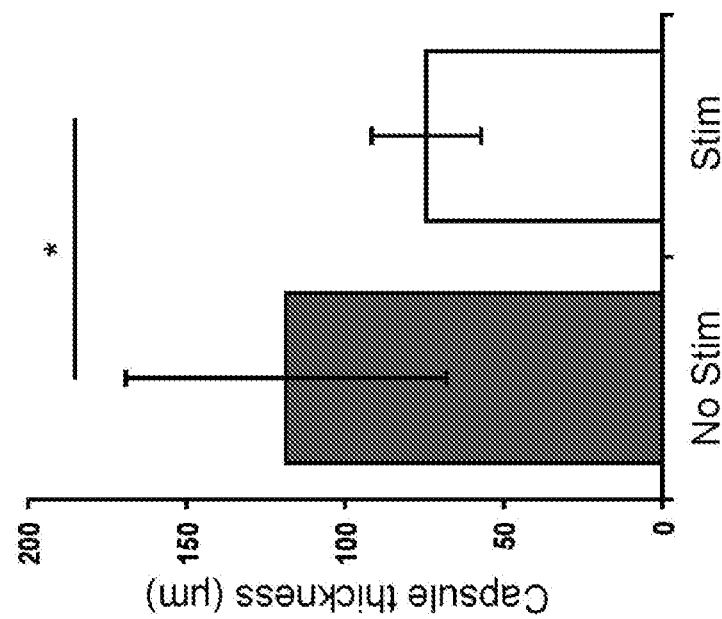

(58) Field of Classification Search
CPC ......... A61L 27/14; A61K 9/0024; A61K 9/06; A61K 35/12; A61K 47/36
See application file for complete search history.

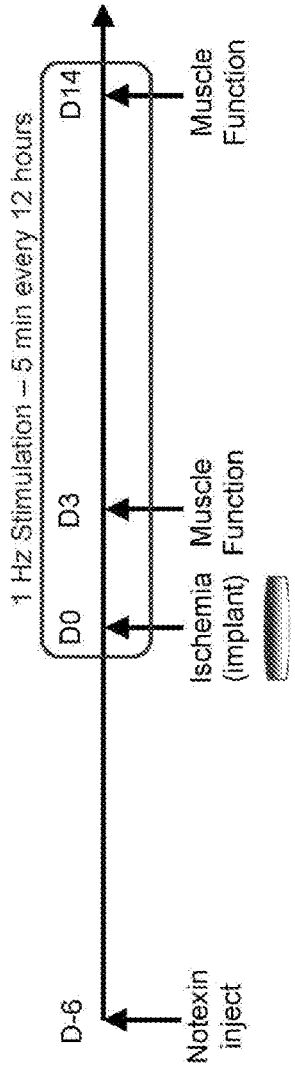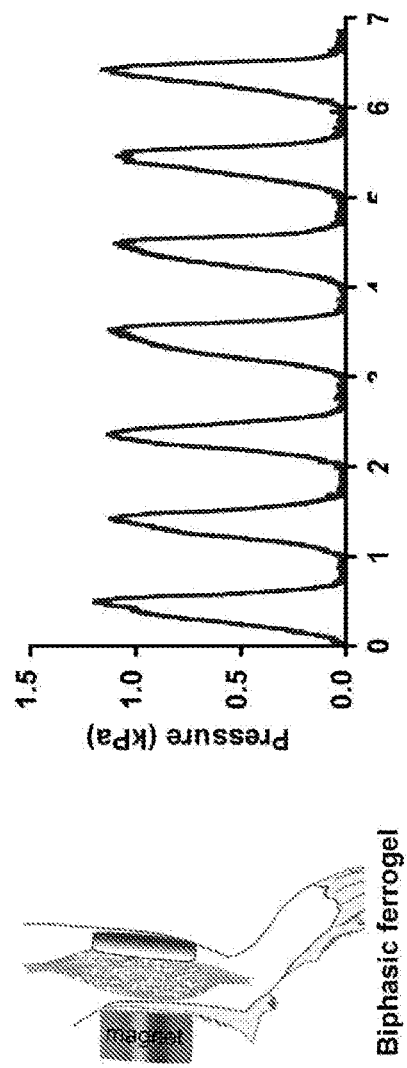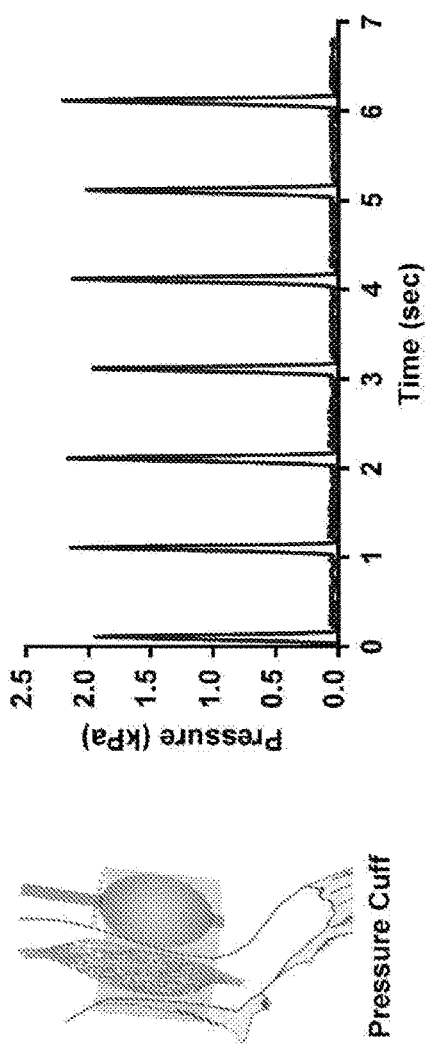
Figure 1A
Figure 1B
Figure 1C

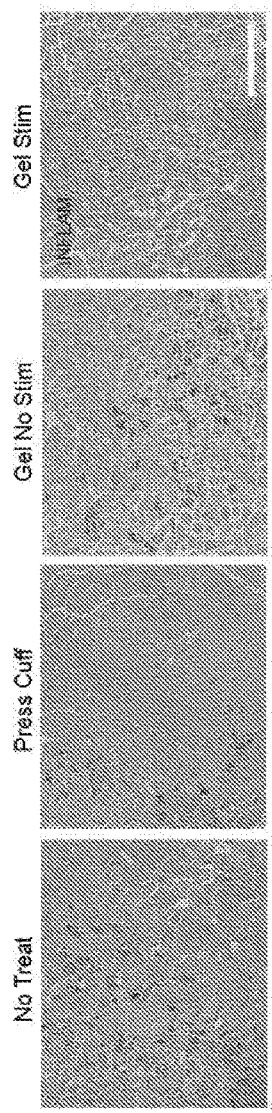
Figure 4A
Figure 4B
Figure 4C
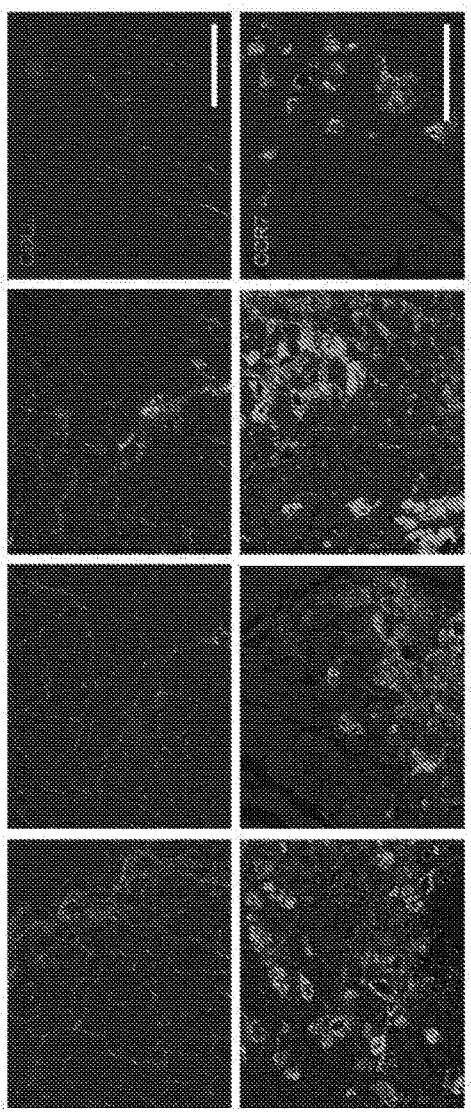
Figure 4D
Figure 4E
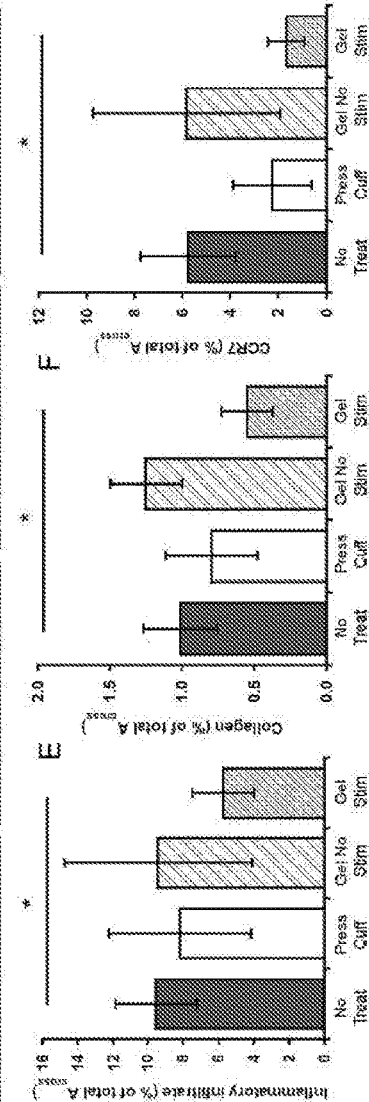
Figure 4F

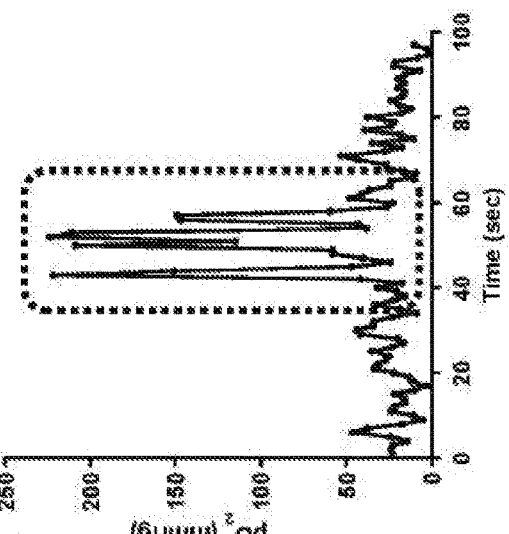
Figure 5A
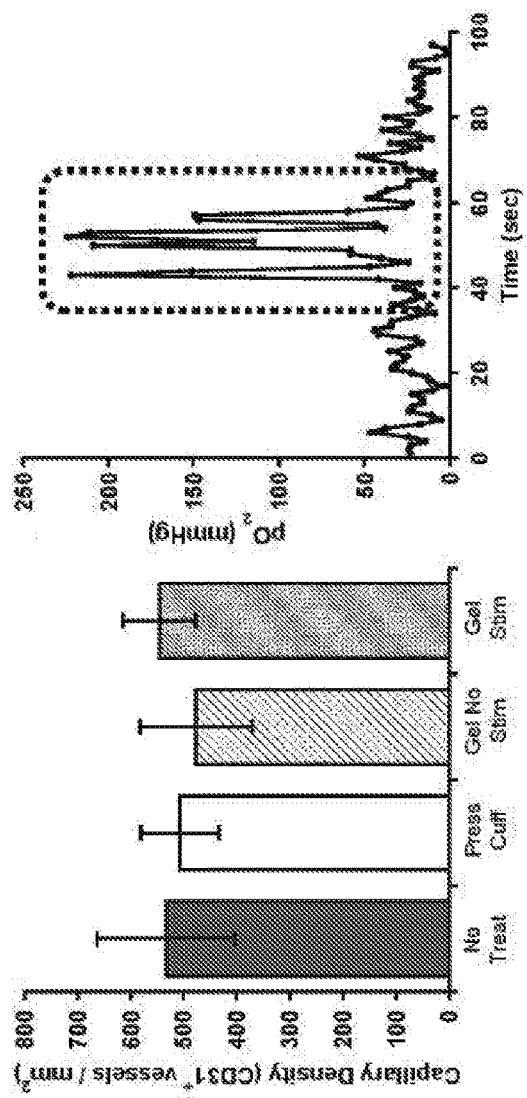
Figure 5B
Figure 5C
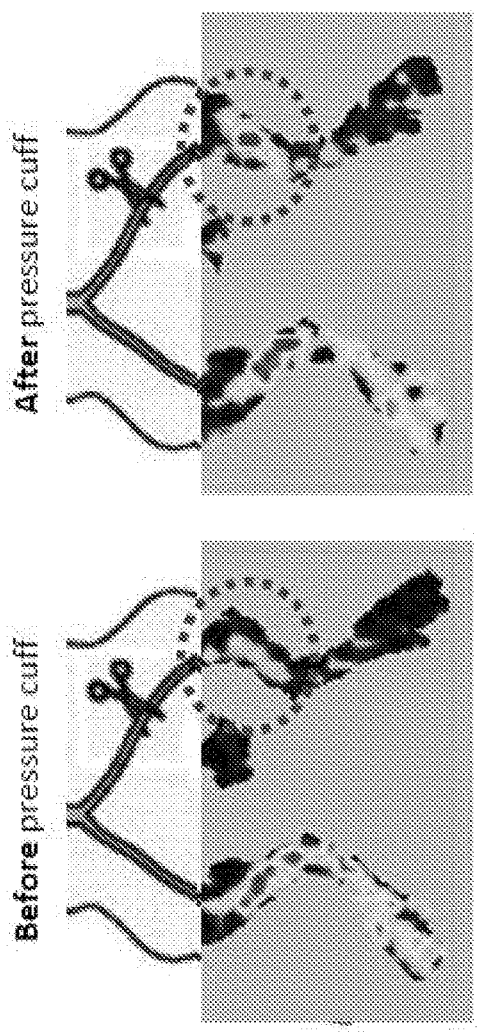
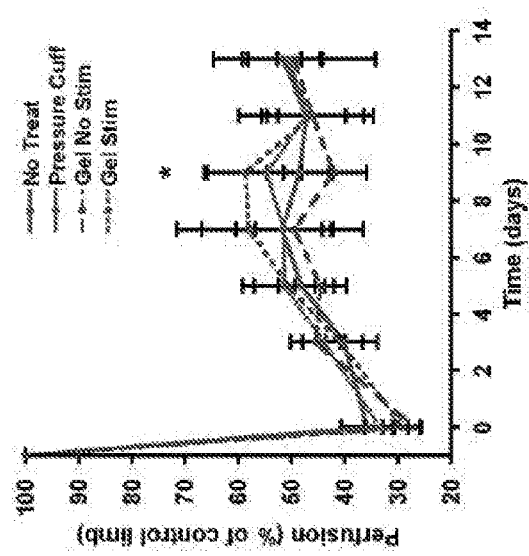
Figure 5D

Figure 10 continued

Proprotein Convertase 9/ PCSK9
Angiopoietin-2
CD14
HGF
CCL6/C10
Pentraxin 2/SAP
IL-23
WISP-1/CCN4
RBP4
Leptin
Complement Factor D
CCL3/CCL4 MIP-1 alpha/beta
Endoglin/CD105
CXCL13/BLC/BCA-1
CXCL11/I-TAC
TNF-alpha
ICAM-1/CD54
IL-22
C1q R1/CD93
IL-4
DKK-1
Endostatin
(Coagulation Factor III/ Tissue Factor
IL-1 alpha/IL-1F1
VCAM-1/CD106
IL-7
LIX
Flt-3 Ligand
IL-28
CCL17/TARC
Fetuin A/AHSG
Chemerin
VEGF
Resistin
LDL R
IL-15
Angiopoietin-like 3
DPPIV/CD26
Gas 6
TIM-1/KIM-1/ HAVCR
CD160

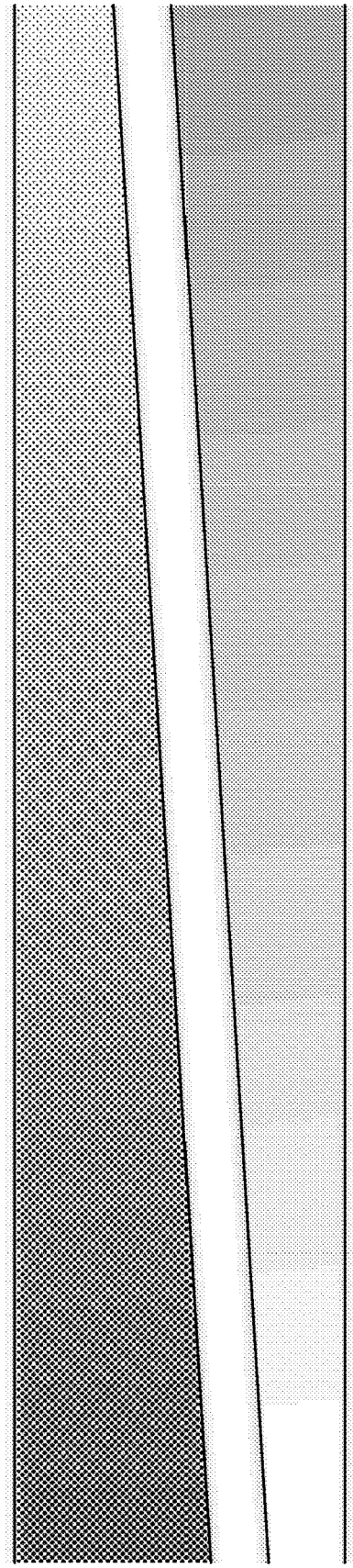

COMPOSITIONS AND METHODS OF MECHANICALLY INDUCING TISSUE REGENERATION

RELATED APPLICATIONS

This application is a 35 U.S.C. § 371 national stage filing of International Application No. PCT/US2016/062685, filed on Nov. 18, 2016, which in turn claims the benefit of priority to U.S. Provisional Application No. 62/256,877, filed on Nov. 18, 2015 and U.S. Provisional Application No. 62/305,323, filed on Mar. 8, 2016. The entire contents of each of the foregoing patent applications are incorporated herein by reference.

GOVERNMENT SUPPORT

The invention was made with government support under DE013349 awarded by National Institutes of Health, DMR-0820484 awarded by National Science of Foundation. The government has certain rights in the invention.

BACKGROUND OF THE INVENTION

Skeletal muscle comprises a large percentage of the human body mass (40-50%) and plays an essential role in locomotion, postural support, and breathing. In response to minor injuries, skeletal muscle possesses a remarkable capacity for regeneration. Small exercise-induced tears, lacerations, and contusions typically heal without therapeutic intervention (Juhas M & Bursac N (2013) *Curr. Opin. Biotechnol.* 24(5):880-886; Turner N J & Badylak S F (2012) *Cell Tissue Res.* 347(3):759-774). However, severe injuries resulting in a muscle mass loss of greater than 20% can lead to extensive fibrosis and loss of muscle function (Turner N J & Badylak S F (2012) *Cell Tissue Res.* 347(3): 759-774). Unfortunately, traumatic injuries resulting from motor vehicle accidents, aggressive tumor ablation, and prolonged denervation are common clinical situations and frequently lead to volumetric muscle loss (Turner N J & Badylak S F (2012) *Cell Tissue Res.* 347(3):759-774; Jarvinen TAHJ, et al. (2005) *Am. J. Sports Med.* 33(5):745-764; Rossi C A, et al. (2010) *Organogenesis* 6(3):167-172). While surgical reconstruction can lead to improved outcomes, this technique typically does not fully regenerate lost muscle tissue and often leads to donor site morbidity (Ma C H, et al. (2008) *Injury* 39 Suppl 4:67-74; Tu Y K, et al. (2008) *Injury* 39 Suppl 4:75-95). As a result, the development of therapeutic strategies to treat severe skeletal muscle injuries is an area of active investigation.

Typical current approaches to skeletal muscle repair rely upon the delivery of biologics such as growth factors and cells to enhance muscle regeneration. In early clinical trials, the intramuscular injection of cultured myoblasts was proven to be a safe but ineffective cell therapy for human myopathies, likely due to rapid death, poor migration, and immune rejection of the donor cells (Tedesco F S & Cossu G (2012) *Curr. Opin. Neurol.* 25(5):597-603; Palmieri B, et al. (2010) *Pediatr. Transplant.* 14(7):813-819). Recently, the identification of several important microenvironmental cues that regulate satellite cell fate has led to the development of cell-instructive biomaterials that improve cell engraftment and muscle regeneration. Biomaterial-based delivery of myogenic (IGF, FGF-2, HGF) and angiogenic factors (VEGF) that appear during the normal regenerative process has proven successful in animal models of severe muscle injury (Ten Broek R W, et al. (2010) *J. Cell. Physiol.* 224(1):7-16; Shansky J, et al. (2006) *Tissue Eng.* 12(7): 1833-1841; Pelosi L, et al. (2007) *FASEB J.* 21(7):1393-1402; Silva E A & Mooney D J (2007) *J. Thromb. Haemost.* 5(3):590-598; Borselli C, et al. (2010) *Proc. Natl. Acad. Sci. U.S.A.* 107(8):3287-3292). Furthermore, the synergistic presentation of cells and growth factors that mimic normal in vivo presentation has led to improved functional muscle regeneration in mice (Borselli C, et al. (2010) *Proc. Natl. Acad. Sci. U.S.A.* 107(8):3287-3292; Sheehan S M & Allen R E (1999) *J. Cell. Physiol.* 181(3):499-506). However, although much progress has been made toward the development of cell and growth factor-based approaches for the treatment of severely injured skeletal muscle in rodents, reliable clinical therapies still do not exist.

Accordingly, there remains an ongoing and unmet need for the development of novel therapeutic strategies to treat severe muscle injuries.

SUMMARY OF THE INVENTION

The present invention is based, at least in part, on the discovery that devices with a capacity to apply cyclic compression forces such as biphasic ferrogels and pressure cuffs can be used to mechanically stimulate and regenerate injured tissue, e.g., muscle tissue, without the use of growth factors or cells. In particular, both magnetic actuation of biphasic ferrogel scaffolds implanted at the site of muscle injury and external actuation of compression device surrounding the site of muscle injury resulted in uniform cyclic compressions that led to reduced fibrous capsule formation around the implant, as well as reduced fibrosis and inflammation in the injured muscle. Furthermore, ferrogel-driven and pressure cuff-driven mechanical compressions led to enhanced muscle regeneration and an approximately 3 and 2.2-fold increase in maximum contractile force of the treated muscle, respectively. Without intending to be limited by theory, it is believed that these biologic-free devices exhibit a potential immunomodulatory role when stimulated and could potentially translate rapidly to the clinic. In addition, the therapeutic use of direct mechanical stimulation of injured tissues via externally actuated compression devices could establish a new paradigm for regenerative medicine.

Accordingly, in one aspect, the present invention provides methods for promoting regeneration of a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, e.g., about 10 µm to 1000 µm, about 50 µm to 1000 µm, about 100 µm to 1000 µm, about 150 µm to 1000 µm, about 200 µm to 1000 µm, about 300 µm to 1000 µm, about 400 µm to 1000 µm, about 500 µm to 1000 µm, about 600 µm to 1000 µm, about 1000 µm to 10000 µm, about 2000 µm to 10000 µm, about 3000 µm to 10000 µm, about 4000 µm to 10000 µm, about 5000 µm to 10000 µm, or about 6000 µm to 10000 µm, wherein the magnetic material is in the form of magnetic particles having a size in the range from about 1 nm to about 500 nm, and wherein porosity, pore size, pore connectivity, swelling agent concentration and/or specific volume of the composition changes by at least 10% in response to an electromagnetic signal; and applying cyclic mechanical compressions to the tissue, thereby promoting regeneration of the tissue.

In some embodiments, the cyclic mechanical compressions are caused by an electromagnetic signal. In other embodiments, the cyclic mechanical compressions are caused by pneumatic or hydraulic actuation.

In some embodiments, the composition comprises a swelling agent. In other embodiments, the composition has a porosity of 0.1 to 0.99.

In some embodiments, the matrix material is a polymer, a copolymer, or a block polymer gel. In other embodiments, the matrix material is a cross-linked polymer, a copolymer, or a block polymer gel. In some embodiments, the matrix material comprises a polymer selected from the group consisting of polyurethanes, glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpo-lactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.

In some embodiments, the magnetic material is ferromagnetic, ferrimagnetic, diamagnetic, paramagnetic, or superparamagnetic material. In other embodiments, the magnetic material is an iron oxide particle. In some embodiments, the iron oxide particle is magnetite. In other embodiments, the iron oxide particle is maghemite.

In some embodiments, the macropores have a mean pore diameter in the range of about 150 μm to about 7500 μm, e.g., about 150 μm to 1000 μm, about 150 μm to 2000 μm, about 150 μm to 3000 μm, about 150 μm to 4000 μm, about 150 μm to 5000 μm, about 150 μm to 6000 μm, about 150 μm to 7000 μm, about 500 μm to 1000 μm, about 600 μm to 1000 μm, about 1000 μm to 2000 μm, 2000 μm to 4000 μm, 3000 μm to 5000 μm, 4000 μm to 6000 μm, or about 5000 μm to 7000 μm.

In some embodiments, the composition comprises a bioactive agent. In other embodiments, the bioactive agent is covalently linked to the matrix material. In some embodiments, the bioactive agent is a therapeutic agent.

In some embodiments, the composition comprises a cell. In other embodiments, the composition is free of a bioactive agent or a cell.

In some embodiments, porosity, pore size, pore connectivity, swelling agent concentration, and/or specific volume changes by at least 25% in response to the electromagnetic signal. In other embodiments, porosity, pore size, pore connectivity, swelling agent concentration, and/or specific volume increases in response to the electromagnetic signal. In yet another embodiment, porosity, pore size, pore connectivity, swelling agent concentration, and/or specific volume decreases in response to the electromagnetic signal.

In some embodiments, the electromagnetic signal is generated by application of a magnetic field.

In some embodiments, the magnetic material is distributed homogeneously within the matrix material. In other embodiments, the magnetic material is distributed heterogeneously within the matrix material. In some embodiments, the heterogeneous distribution of the magnetic material within the matrix material is formed by application of a magnetic field during polymerization of the matrix material. In other embodiments, the magnetic material is distributed into a separate compartment within the matrix material. In yet another embodiment, the magnetic material is distributed at one side within the matrix material distant from the electromagnetic signal.

In some embodiments, the composition is suitable for implantation within the tissue. In some embodiments, the tissue is selected from the group consisting of a muscle tissue, a heart tissue, a blood vessel tissue, a skin tissue, a bone tissue, a cartilage tissue, a connective tissue, a tendon tissue, and a ligament tissue.

In some embodiments, the tissue is a muscle tissue. In other embodiments, the muscle tissue is selected from the group consisting of a skeletal muscle tissue, a smooth muscle tissue and a cardiac muscle tissue.

In some embodiments, the muscle tissue in the subject is damaged. In other embodiments, the muscle tissue damage is induced by exercise. In some embodiments, the muscle tissue damage is induced by a myotoxin. In other embodiments, the muscle tissue damage is induced by ischemia. In some embodiments, the muscle tissue damage is induced by hind limb ischemia. In other embodiments, the muscle tissue damage is induced by a physical trauma. In some embodiments, the muscle tissue damage is induced by cryo-damages. In other embodiments, the muscle tissue damage is induced by muscle degeneration. In some embodiments, the muscle tissue damage is induced by age-related muscle loss. In other embodiments, the muscle tissue damage results in a muscle mass loss or injury of about 0.01% to 99.9%, e.g., a muscle mass loss or injury of greater than 0.1%, 1%, 2%, 3%, 4%, 5%, 6%, 7%, 8%, 9%, 10%, 20%, 30%, 40%, 50%, 60%, 70%, or 90%. In some embodiments, the muscle tissue damage results in a muscle mass loss or injury of greater than 20%.

In some embodiments, the composition is implanted at the site of tissue damage. In other embodiments, the cyclic mechanical compressions are applied to the site of tissue damage after the damage has occurred.

In some embodiments, the cyclic mechanical compressions are applied to the site of tissue damage immediately after the damage has occurred, or within less than 5, 10, 20, 30, 40, 50, 60 minutes after the damage has occurred. In other embodiments, the cyclic mechanical compressions are applied to the site of tissue damage at least 1, 2, 3, 4, 5, 6, 7, 8, 9, 10, 12 or 24 hours after the damage has occurred. In some embodiments, the cyclic mechanical compressions are applied to the site of tissue damage at least 1, 2, 3, 4, 5, 6, 7, 8, 9, 10 days or at least 1, 2, 3, 4, 5, 6, 7, 8, 9, 10 11, 12, 24, 48 or 60 months after the damage has occurred.

In some embodiments, the cyclic mechanical compressions are applied to the site of tissue damage over a period of time. In other embodiments, the cyclic mechanical compressions are applied to the site of tissue damage for at least 1, 2, 3, 4, 5, 6, 7, 8, 9, 10, 11, 12, 24, 36, 48, 60, 72, 84, 96 or 120 hours. In some embodiments, the cyclic mechanical compressions are applied at least once daily.

In some embodiments, the cyclic mechanical compressions are applied to the site of tissue damage for about 1 to 30 days, about 1 to 50 days, about 1 to 100 days, about 1 to 200 days or about 1 to 300 days. In other embodiments, the cyclic mechanical compressions are applied to the site of tissue damage over a period of at least 14 days, e.g., at least 15, 16, 17, 18, 19, 20, 25, 30, 35, 40, 45, 50, 55, 60, 65, 70, 75, 80, 85, 90, 95 or 100 days.

In some embodiments, the methods further comprises determining the level of a cytokine in a subject.

In some embodiments, the subject is a mammal. In other embodiments, the subject is a mammal selected from the group consisting of a human, a horse, a dog, a cat, a cow, a mouse, a rabbit, and a rat.

In one aspect, the present invention provides methods of increasing a mass of a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by at least 10% in response to an electromagnetic signal; and applying cyclic mechanical compressions to the tissue, thereby increasing the mass of the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is a muscle tissue.

In another aspect, the present invention provides methods of enhancing a function of a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by at least 10% in response to an electromagnetic signal; and applying cyclic mechanical compressions to the tissue, thereby enhancing the function of the tissue.

In some embodiments, the cyclic mechanical compressions are caused by the electromagnetic signal. In other embodiments, the cyclic mechanical compressions are caused by pneumatic or hydraulic actuation.

In some embodiments, the tissue is a muscle tissue. In other embodiments, the contractile force of the tissue is increased.

In one aspect, the present invention provides methods for preventing or reducing inflammation of a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by at least 10% in response to an electromagnetic signal; and applying cyclic mechanical compressions to the tissue, thereby preventing or reducing inflammation of the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is damaged in the subject. In some embodiments, the tissue is a muscle tissue.

In some embodiments, the composition is implanted at a site of tissue damage. In other embodiments, fibrosis at the site of tissue damage is reduced. In some embodiments, inflammatory cell removal at the site of tissue damage is accelerated.

In some embodiments, the methods comprise determine the level of a cytokine in a subject is increased. In other embodiments, the level of a cytokine in a subject is reduced. In some embodiments, the level of a pro-inflammatory cytokine in a subject is reduced. In other embodiments, the pro-inflammatory cytokine is selected from the group consisting of myeloperoxidase, neutrophil gelatinase-associated lipocalin, interleukin-17A and interleukin-6. In other embodiments, the level of a pro-inflammatory cytokine in a subject is reduced by enhanced intramuscular convection driven by cyclic mechanical compressions of the muscle tissue.

In another aspect, the present invention provides methods of preventing or reducing fibrosis of a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by promoting at least 10% in response to an electromagnetic signal; and applying cyclic mechanical compressions to the tissue, thereby preventing or reducing fibrosis of the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is damaged. In some embodiments, the tissue is a muscle tissue.

In some embodiments, the composition is implanted at a site of tissue damage. In other embodiments, the formation of a fibrous capsule at the site of tissue damage is reduced. In some embodiments, the thickness of the fibrous capsule at the site of tissue damage is reduced. In other embodiments, inflammatory cell removal at the site of tissue damage is accelerated.

In one aspect, the present invention provides methods of increasing a level of oxygen available to a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by promoting at least 10% in response to an electromagnetic signal; and applying cyclic mechanical compressions to the tissue, thereby increasing the level of oxygen available to the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is a muscle tissue. In some embodiments, the oxygen level is increased by increasing blood flow to the muscle tissue. In other embodiments, the oxygen level is increased by enhanced intramuscular convection driven by cyclic mechanical compressions of the muscle tissue.

In another aspect, the present invention provides methods of increasing a rate of metabolic waste product removal from a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by promoting at least 10% in response to an electromagnetic signal; and applying cyclic mechanical compressions to the tissue, thereby increasing the rate of metabolic waste product removal from the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is a muscle tissue. In some embodiments, the rate of metabolic waste product removal is increased by enhanced fluid transportation driven by cyclic mechanical compressions around the tissue.

In one aspect, the present invention provides methods of increasing blood perfusion to a tissue in a subject in need thereof. The methods include contacting the tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by promoting at least 10% in response to an electromagnetic signal; and applying cyclic mechanical compressions to the tissue, thereby increasing blood perfusion to the tissue.

In some embodiments, the cyclic mechanical compressions are caused by an electromagnetic signal. In other embodiments, the cyclic mechanical compressions are caused by pneumatic or hydraulic actuation.

In some embodiments, the tissue is a muscle tissue.

In one aspect, the present invention provides methods of treating a severe muscle tissue damage in a subject in need thereof. The methods include contacting the muscle tissue with a composition comprising a matrix material and a magnetic material distributed therethrough, wherein the composition comprises macropores having a mean pore diameter in the range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition changes by promoting at least 10% in response to an electromagnetic signal; and applying cyclic mechanical compressions to the muscle tissue, thereby treating the severe muscle tissue damage in the subject.

In some embodiments, the cyclic mechanical compressions are caused by an electromagnetic signal. In other embodiments, the cyclic mechanical compressions are caused by pneumatic or hydraulic actuation.

In one aspect, the present invention provides methods for promoting regeneration of a tissue in a subject in need thereof. The methods include contacting the tissue with a compression device suitable for applying cyclic mechanical compressions at a site of tissue damage, and applying cyclic mechanical compressions to the tissue using the compression device, thereby promoting regeneration of the tissue at the site of tissue damage.

In some embodiments, the site of tissue damage is on or in a limb, a spine, a neck, a waist, a shoulder, a knee, or a joint of the subject. In some embodiments, the limb is a lower limb of the subject and the site of the tissue damage is on or in an ankle, a calf, a thigh, or a foot. In other embodiments, the limb is a upper limb of the subject is and the site of the tissue damage is on or in a hand, a wrist, an arm, a shoulder or an axilla.

In some embodiments, the compression device is electromagnetically actuated, pneumatically actuated or hydraulically actuated to apply the cyclic mechanical compressions to the tissue.

In some embodiments, the compression device comprises a surrounding member configured to surround the site of tissue damage and apply compression to the site of the tissue damage. In some embodiments, contacting the tissue with the compression device suitable for applying cyclic mechanical compressions at the site of tissue damage comprises disposing the surrounding member encircling a body part that includes the site of tissue damage. In some embodiments, the surrounding member is disposed externally to the body and encircling the body part. In other embodiments, the surrounding member is disposed at least partially internally within the body and encircling the body part.

In some embodiments, applying cyclic mechanical compressions to the tissue using the compression device comprises using a controller associated with the surrounding member to generate the cyclic mechanical compressions in the surrounding member.

In some embodiments, the compression device further comprises the controller. In some embodiments, the controller is programmable to achieve different motions and forces; and wherein the method further comprises selecting a desired motion or a desired force using the controller prior to or during applying cyclic mechanical compressions to the tissue using the compression device. In some embodiments, the desired motion comprises one or more of bending, twisting or squeezing.

In some embodiments, the surrounding member comprises a soft actuator; and wherein the cyclic mechanical compressions are applied to the tissue, at least in part, by actuation of the soft actuator. In other embodiments, the surrounding member further comprises an inflatable portion having a channel; and wherein the soft actuator is disposed in the channel.

In some embodiments, the soft actuator is selected from the group consisting of a fiber reinforced actuator, a Pneunet bending actuator, a McKibben actuator, a pleated air muscle, a balloon, an inflatable device, a motor, a vibrating motor, a cable, an electroactive material, e.g., a shape memory alloy, an electrostatic, a dielectric elastomer, and combinations thereof.

In some embodiments, the surrounding member comprises one or more inflatable portions. In other embodiments, the one or more inflatable portions comprise one or more inflatable members. In some embodiments, the one or more inflatable members comprise a balloon; and wherein the surrounding member further comprises a sleeve comprising a textile, a mesh, a fabric, a silicone elastomer or a rubber configured to hold the balloon against a site of tissue damage.

In some embodiments, applying cyclic mechanical compressions to the tissue using the compression device comprises adjusting an inflation pressure of at least some of the one or more inflatable portions using a controller associated with the surrounding member.

In some embodiments, contacting the tissue with a compression device suitable for applying cycle mechanical compressions at the site of tissue damage comprises at least partially inflating at least some of the one or more inflatable portions or increasing an inflation pressure applied to the one or more inflatable portions.

In some embodiments, the one or more inflatable portions comprise a plurality of independently inflatable portions. In some embodiments, applying cyclic mechanical compressions to the tissue using the compression device comprises individually controlling an inflation pressure of each of the independently inflatable portions using the controller associated with the surrounding member. In other embodiments, the cyclic mechanical compressions are applied to only a portion of the tissue underlying the surrounding member, wherein the portion of the tissue is at, overlies or is adjacent to the site of tissue damage.

In some embodiments, the compression device is configured to be customizable for different geometries and morphologies. In other embodiments, the compression device is suitable for wearable applications; and wherein the subject is wearing the compression device while the cyclic mechanical compressions are applied to the tissue.

In some embodiments, the compression device is suitable for generating active cyclic mechanical compressions.

In some embodiments, the composition is suitable for implantation within the tissue. In some embodiments, the tissue is selected from the group consisting of a muscle tissue, a heart tissue, a blood vessel tissue, a skin tissue, a bone tissue, a cartilage tissue, a connective tissue, a tendon tissue, and a ligament tissue.

In some embodiments, the tissue is a muscle tissue. In other embodiments, the muscle tissue is selected from the group consisting of a skeletal muscle tissue, a smooth muscle tissue and a cardiac muscle tissue.

In some embodiments, the muscle tissue in the subject is damaged. In other embodiments, the muscle tissue damage is induced by exercise. In some embodiments, the muscle tissue damage is induced by a myotoxin. In other embodiments, the muscle tissue damage is induced by ischemia. In some embodiments, the muscle tissue damage is induced by hind limb ischemia. In other embodiments, the muscle tissue damage is induced by a physical trauma. In some embodiments, the muscle tissue damage is induced by cryo-damages. In other embodiments, the muscle tissue damage is induced by muscle degeneration. In some embodiments, the muscle tissue damage is induced by age-related muscle loss. In other embodiment, the muscle tissue damage results in a muscle mass loss or injury of about 0.01% to 99.9%, e.g., a muscle mass loss or injury of greater than 0.1%, 1%, 2%, 3%, 4%, 5%, 6%, 7%, 8%, 9%, 10%, 20%, 30%, 40%, 50%, 60%, 70%, or 90%. In some embodiments, the muscle tissue damage results in a muscle mass loss or injury of about greater than 20%.

In some embodiments, the composition is implanted at the site of tissue damage. In other embodiments, the cyclic mechanical compressions are applied to the site of tissue damage after the damage has occurred.

In some embodiments, the cyclic mechanical compressions are applied to the site of tissue damage immediately after the damage has occurred, or within less than 5, 10, 20, 30, 40, 50, 60 minutes after the damage has occurred. In other embodiments, the cyclic mechanical compressions are applied to the site of tissue damage at least 1, 2, 3, 4, 5, 6, 7, 8, 9, 10, 12 or 24 hours after the damage has occurred. In some embodiments, the cyclic mechanical compressions are applied to the site of tissue damage at least 1, 2, 3, 4, 5, 6, 7, 8, 9, 10 days or at least 1, 2, 3, 4, 5, 6, 7, 8, 9, 10 11, 12, 24, 48 or 60 months after the damage has occurred.

In some embodiments, the cyclic mechanical compressions are applied to the site of tissue damage over a period of time. In other embodiments, the cyclic mechanical compressions are applied to the site of tissue damage for at least 1, 2, 3, 4, 5, 6, 7, 8, 9, 10, 11, 12, 24, 36, 48, 60, 72, 84, 96 or 120 hours. In some embodiments, the cyclic mechanical compressions are applied at least once daily.

In some embodiments, the cyclic mechanical compressions are applied to the site of tissue damage for about 1 to 30 days, about 1 to 50 days, about 1 to 100 days, about 1 to 200 days or about 1 to 300 days. In other embodiments, the cyclic mechanical compressions are applied to the site of tissue damage over a period of at least 14 days, e.g., at least 15, 16, 17, 18, 19, 20, 25, 30, 35, 40, 45, 50, 55, 60, 65, 70, 75, 80, 85, 90, 95 or 100 days.

In some embodiments, the compression device is configured to exert a peak pressure of about 0.1 kPa to 1000 kPa, about 1-10 kPa, about 1-20 kPa, about 1-30 kPa, about 1-50 kPa, about 1-100 kPa, about 1-1000 kPa, about 10-100 kPa, about 10-200 kPa, about 10-300 kPa, about 10-500 kPa, about 10-1000 kPa, about 100-1000 kPa, about 200-1000 kPa, about 300-1000 kPa, about 400-1000 kPa, about 500-1000 kPa, about 600-1000 kPa, about 700-1000 kPa, about 800-1000 kPa, or about 900-1000 kPa.

In some embodiments, the subject is a mammal. In other embodiments, the subject is a mammal selected from the group consisting of a human, a horse, a dog, a cat, a cow, a mouse, a rabbit, and a rat.

In one aspect, the present invention provides methods for preventing or reducing inflammation of a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby preventing or reducing inflammation of the tissue.

In some embodiments, the tissue is a muscle tissue. In other embodiments, fibrosis at the site of tissue damage is reduced. In some embodiments, inflammatory cell removal at the site of tissue damage is accelerated.

In some embodiments, the methods comprise determine the level of a cytokine in a subject is increased. In other embodiments, the level of a cytokine in a subject is reduced. In some embodiments, the level of a pro-inflammatory cytokine in a subject is reduced. In other embodiments, the pro-inflammatory cytokine is selected from the group consisting of myeloperoxidase, neutrophil gelatinase-associated lipocalin, interleukin-17A and interleukin-6. In other embodiments, the level of a pro-inflammatory cytokine in a subject is reduced by enhanced intramuscular convection driven by cyclic mechanical compressions of the muscle tissue.

In another aspect, the present invention provides methods of preventing or reducing fibrosis of a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby preventing or reducing fibrosis of the tissue.

In some embodiments, the tissue is a muscle tissue. In other embodiments, the formation of a fibrous capsule at the site of tissue damage is reduced. In some embodiments, the thickness of the fibrous capsule at the site of tissue damage is reduced. In other embodiments, inflammatory cell removal at the site of tissue damage is accelerated.

In one aspect, the present invention provides methods of increasing a mass of a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby increasing the mass of the tissue.

In some embodiments, the tissue is a muscle tissue.

In another aspect, the present invention provides methods of enhancing a function of a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby enhancing the function of the tissue.

In some embodiments, the tissue is a muscle tissue. In other embodiments, the contractile force of the tissue is increased.

In one aspect, the present invention provides methods of increasing a level of oxygen available to a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby increasing the level of oxygen available to the tissue.

In some embodiments, the tissue is a muscle tissue. In some embodiments, the oxygen level is increased by increasing blood flow to the muscle tissue. In other embodiments, the oxygen level is increased by enhanced intramuscular convection driven by cyclic mechanical compressions of the muscle tissue.

In another aspect, the present invention provides methods of increasing a rate of metabolic waste product removal from a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby increasing the rate of metabolic waste product removal from the tissue.

In some embodiments, the tissue is a muscle tissue. In some embodiments, the rate of metabolic waste product removal is increased by enhanced fluid transportation driven by cyclic mechanical compressions around the tissue.

In one aspect, the present invention provides methods of increasing blood perfusion to a tissue in a subject in need thereof. The methods include contacting the tissue with a compression device suitable for applying cyclic mechanical compressions at a site of tissue damage, and applying cyclic mechanical compressions to the tissue using the compression device using the compression device, thereby increasing blood perfusion to the tissue.

In some embodiments, the tissue is a muscle tissue.

In one aspect, the present invention provides methods of treating a severe muscle tissue damage in a subject in need thereof. The methods include contacting the muscle tissue with a compression device suitable for applying cyclic mechanical compressions at a site of muscle tissue damage, and applying cyclic mechanical compressions to the muscle tissue using the compression device using the compression device, thereby treating a severe muscle tissue damage in the subject.

In one aspect, the present invention provides wearable compression devices for promoting regeneration of a tissue in a subject. The devices comprise a surrounding member configured to encircle a body part including a site of tissue damage and apply cyclic mechanical compressions to the tissue at the site of tissue damage; and a controller configured to generate the cyclic mechanical compressions in the surrounding member.

In some embodiments, the controller comprises a microcontroller configured to control one or more of the following: a frequency of compression cycles, a total duration of compression cycles, a length of a period of increasing compression in a single cycle, a length of a period of decreasing compression in a single cycle, or a peak compression level.

In some embodiments, the surrounding member includes one or more inflatable portions. In other embodiments, the one or more inflatable portions include one or more of a balloon, a bladder or an independently inflatable member.

In some embodiments, the controller further comprises a pump configured to provide fluid in the form of a liquid or a gas to at least some of the one or more inflatable portions of the surrounding member.

In some embodiments, the controller further comprises a valve configured to control fluid flow between the pump and at least some of the one or more inflatable portions of the surrounding member, wherein the valve is controlled by the microcontroller.

In some embodiments, the devices further comprise a pressure sensor disposed in or on the surrounding member configured to be positioned between at least one of the one or more inflatable portions of the surrounding member and the site of tissue damage, the pressure sensor in communication with the microcontroller.

In some embodiments, the controller includes storage configured to store information from a pressure sensor regarding a plurality of pressure measurements during application of cyclic mechanical compressions to tissue of a subject.

In other embodiments, the controller includes storage storing machine readable instructions for: applying an inflation pressure to at least some of the one or more inflatable portions of the surrounding member to generate the cyclic mechanical compressions in the surrounding member; receiving information regarding a pressure measurement from the pressure sensor; and modifying one or both of a level of the inflation pressure applied or a time period that the inflation pressure is applied to at least some of the one or more inflatable portions based on the information regarding a pressure measurement received from the pressure sensor.

In some embodiments, the controller includes storage storing machine readable instructions for cyclically applying an inflation pressure to at least some of the one or more inflatable portions of the surrounding member to generate the cyclic mechanical compressions in the surrounding member.

In some embodiments, the surrounding member comprises one or more soft actuators. In some embodiments, the one or more soft actuators include one or more of a fiber reinforced actuator, a Pneunet bending actuator, a McKibben actuator, or a pleated air muscle.

In some embodiments, the surrounding member further comprises an inflatable portion having a channel, and wherein at least one of the one or more soft actuators is configured to be disposed in the channel.

In some embodiments, the compression device is configured to apply the cyclic mechanical compressions to the tissue while being worn and is self-contained.

The present invention is illustrated by the following drawings and detailed description, which do not limit the scope of the invention described in the claims.

BRIEF DESCRIPTION THE DRAWINGS

FIGS. 1A-C depict the cyclic mechanical compressions generated by biphasic ferrogels and pressure cuffs. Specifically, FIG. 1A depicts the experimental design showing injury, implant, and stimulation profile. FIG. 1B depicts the schematic of biphasic ferrogel implant in mouse hindlimb showing orientation of ferrogel relative to skin, muscle tissue, and magnet (left). Pressure profile of biphasic ferrogel undergoing repeated magnetic stimulations (right). FIG. 1C depicts the schematic of pressure cuff on mouse hindlimb showing orientation of balloon and polycarbonate cuff relative to skin and muscle tissue (left). Pressure profile of balloon cuff undergoing repeated inflations and deflations (right).

Figure 2A:
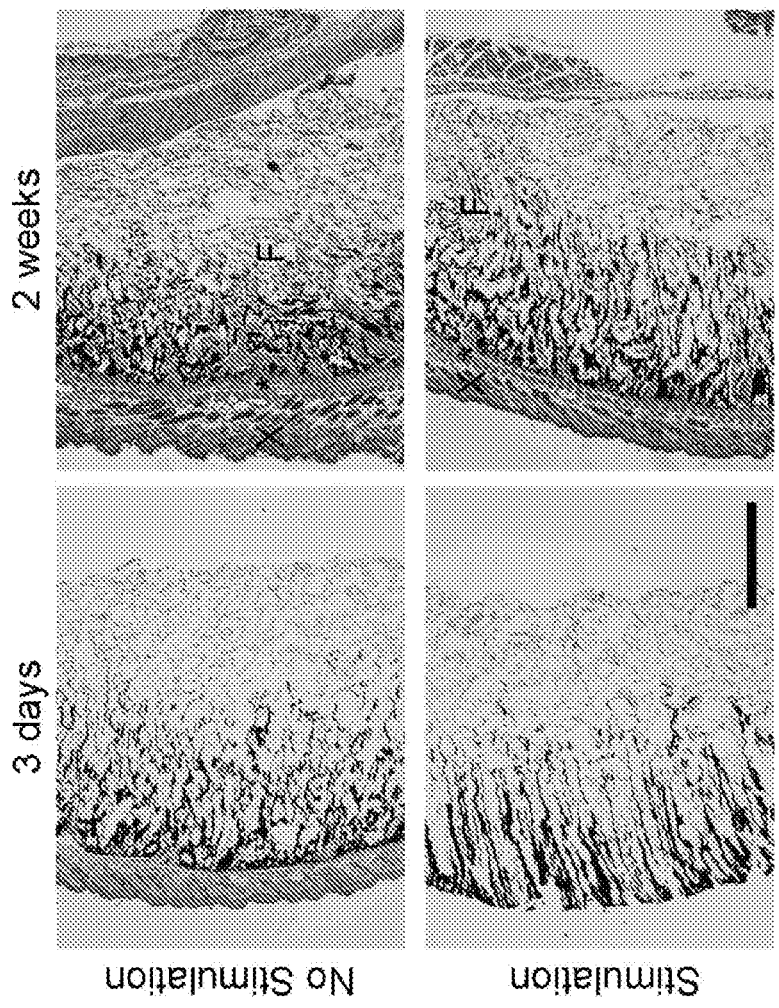

FIGS. 2A and 2B depict that magnetic stimulation of ferrogel implants decreases fibrous capsule thickness. Specifically, FIG. 2A depicts the cross-sections of biphasic ferrogels stained with hematoxylin and eosin at 3 days and 2 weeks following implantation. Skin (X), fibrous capsule (*), and ferrogels (F) are indicated. It is important to note that significant fibrous capsule formation was not observed at 3 days in either ferrogel condition and surrounding tissues were often lost during processing. FIG. 2B depicts quantified fibrous capsule thickness of non-stimulated and stimulated biphasic ferrogels following 2 weeks of implantation. Fibrous capsule boundaries are marked with red dashed lines in FIG. 2A. Scale bar represents 500 µm. Data were compared using a two-tailed unpaired Student's t-test with Welch's correction (N=9, *p<0.05). Error bars represent standard deviations.

Figure 3B:
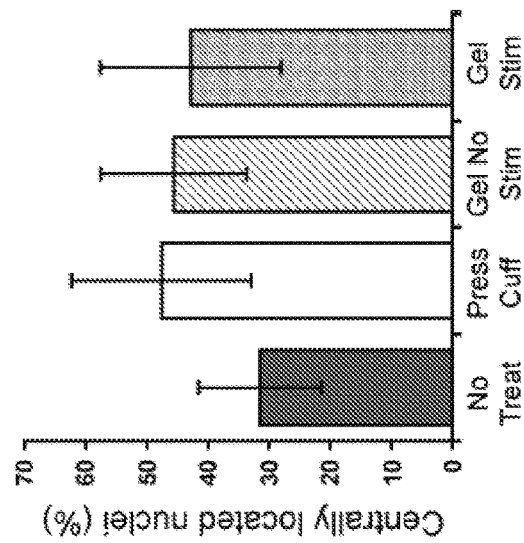
Figure 3C:
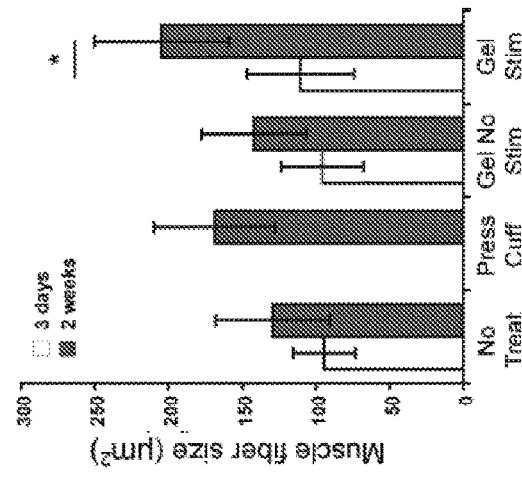
Figure 3A:
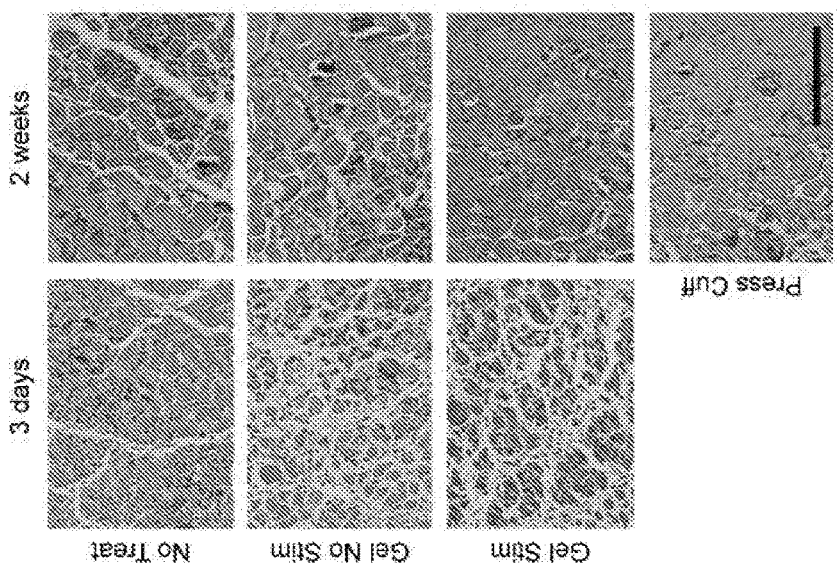

FIGS. 3A-C depict that ferrogel stimulation leads to improved muscle regeneration. Specifically, FIG. 3A depicts histological cross-sections of tibialis anterior muscles stained with hematoxylin and eosin 3 days and 2 weeks following no treatment (No Treat), treatment with a pressure cuff (Press Cuff), treatment with a non-stimulated biphasic ferrogel (Gel No Stim), or treatment with a stimulated biphasic ferrogel (Gel Stim). Scale bar represents 100 m. FIG. 3B depicts quantification of myofibers residing in the defect containing centrally located nuclei 2 weeks post-treatment. Values are expressed as a percentage of the total number of myofibers in the defect. FIG. 3C depicts quantified mean muscle fiber size in the defect area 3 days and 2 weeks post-treatment. Data were compared using ANOVA with Bonferroni's post-hoc test (N=5, *p<0.05). Error bars represent standard deviations.

FIGS. 4A-F depict that ferrogel stimulation decreases inflammation and fibrosis. Specifically, FIGS. 4A and 4D depict representative images and quantification of the inflammatory infiltrate (INFLAM) in histological cross-sections of tibialis anterior muscles stained with hematoxylin and eosin 2 weeks post-treatment. FIGS. 4B and 4E depict representative images and quantification of tissue collagen (COLL) from picosirius red stained cross-sections 2 weeks post-treatment. FIGS. 4C and 4F depict representative images and quantification of M1 macrophages from CCR7 stained cross-sections 2 weeks post-treatment. All values are expressed as a percentage of the total cross-section area ($A_{cross}$) of the tissue section. All scale bars represent 200 µm. Data were compared using ANOVA with Bonferroni's post-hoc test (N=10, *p<0.05) in FIG. 4D and Dunnet's post-hoc test (N=5, *p<0.05) in FIGS. 4E and 4F. Error bars represent standard deviations.

FIGS. 5A-D depict that intramuscular oxygen concentration increases during ferrogel and pressure cuff stimulation. Specifically, FIG. 5A depicts quantified perfusion of injured hindlimbs normalized to contralateral controls, as measured by Laser doppler perfusion imaging (LDPI). A difference between the stimulated and non-stimulated biphasic ferrogel conditions appeared at day 9 is indicated with a (*). FIG. 5B depicts quantified capillary density in injured muscle, as assessed by CD31+ staining 2 weeks post-treatment. FIG. 5C depicts representative oxygen probe trace with stimulation period marked by a dashed line. FIG. 5D depicts the LPCI images of perfusion of injured hindlimbs before (left) and after (right) treatment of pressure cuff. Data were compared using ANOVA with Bonferroni's post-hoc test (N=5, *p<0.05). Error bars represent standard deviations.

Figure 6:
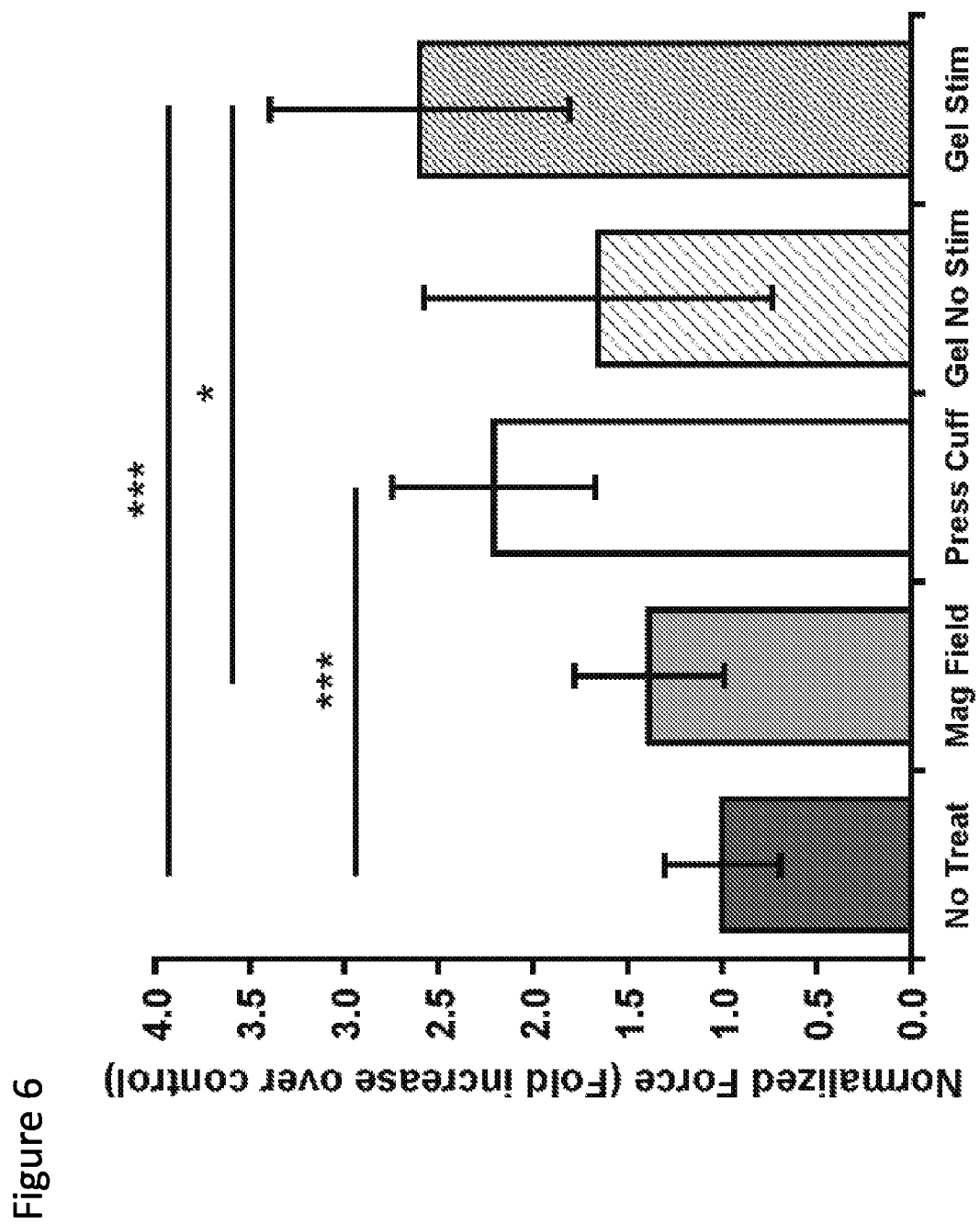

FIG. 6 depicts that cyclic mechanical compressions enhance functional muscle regeneration. Maximum contractile force following tetanic stimulation of injured muscles 2 weeks post-treatment. Force measurements were normalized to muscle wet weight. Data were compared using ANOVA with Dunnet's post-hoc test (N=5-10, *p<0.05, ***p<0.001).

Figure 7B:
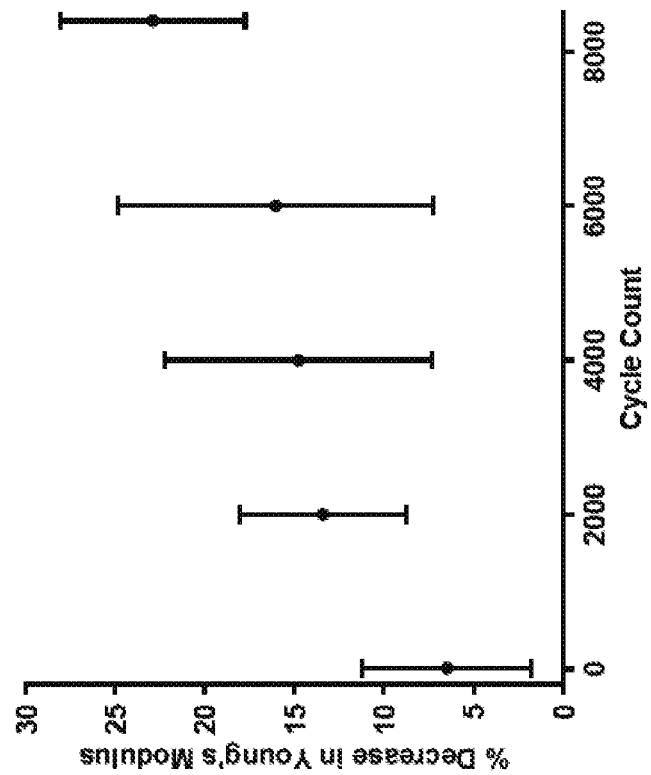
Figure 7A:
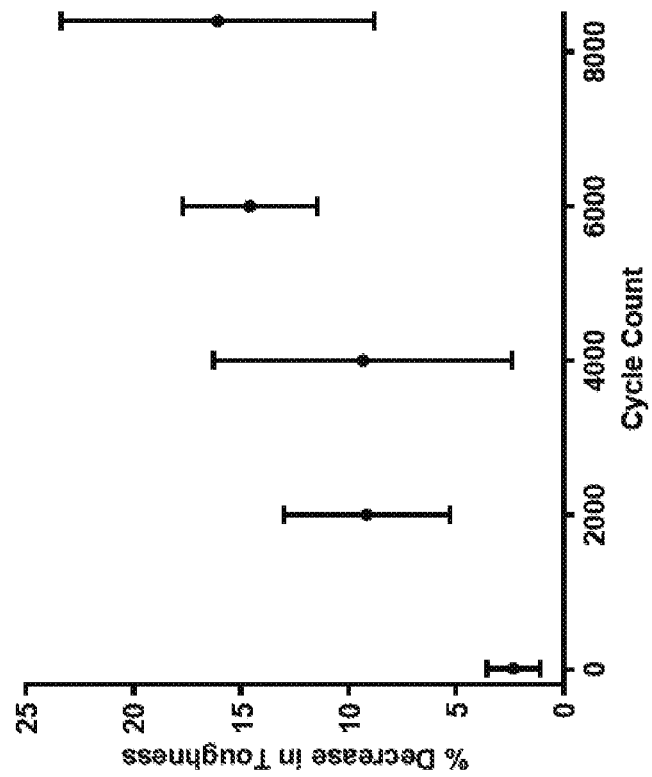

FIGS. 7A and 7B depict that the biphasic ferrogels exhibit fatigue-resistance. Percent decrease in biphasic ferrogel (FIG. 7A) Young's modulus and (FIG. 7B) toughness at 50% strain following 8400 cyclic compressions to 50% strain, as compared with the values calculated from the first cycle of compression. Values represent the mean and standard deviation (N=4).

Figure 8:
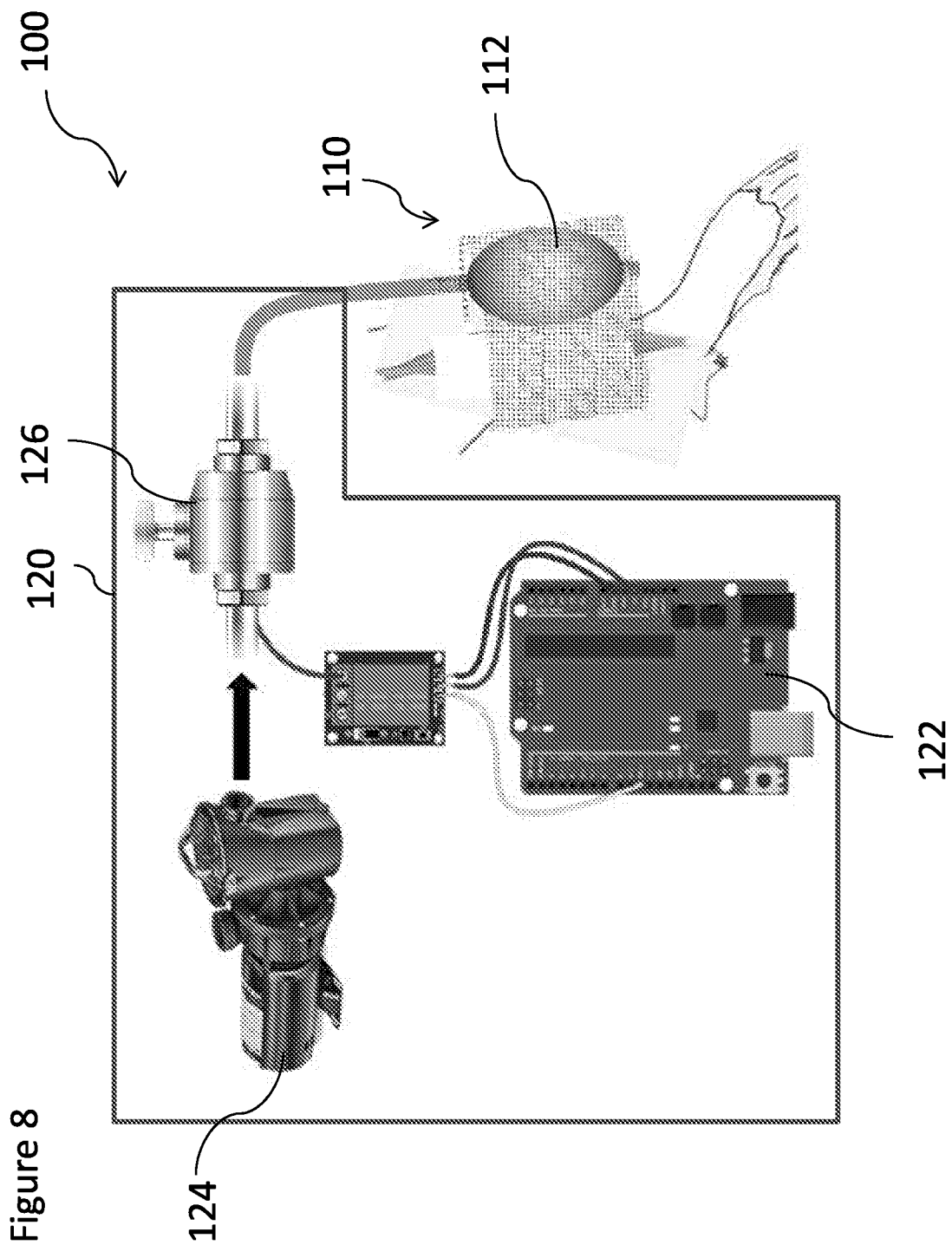

FIG. 8 depicts a schematic for a compression device including a pump, a valve, a microcontroller, a sleeve and a balloon.

Figure 9:
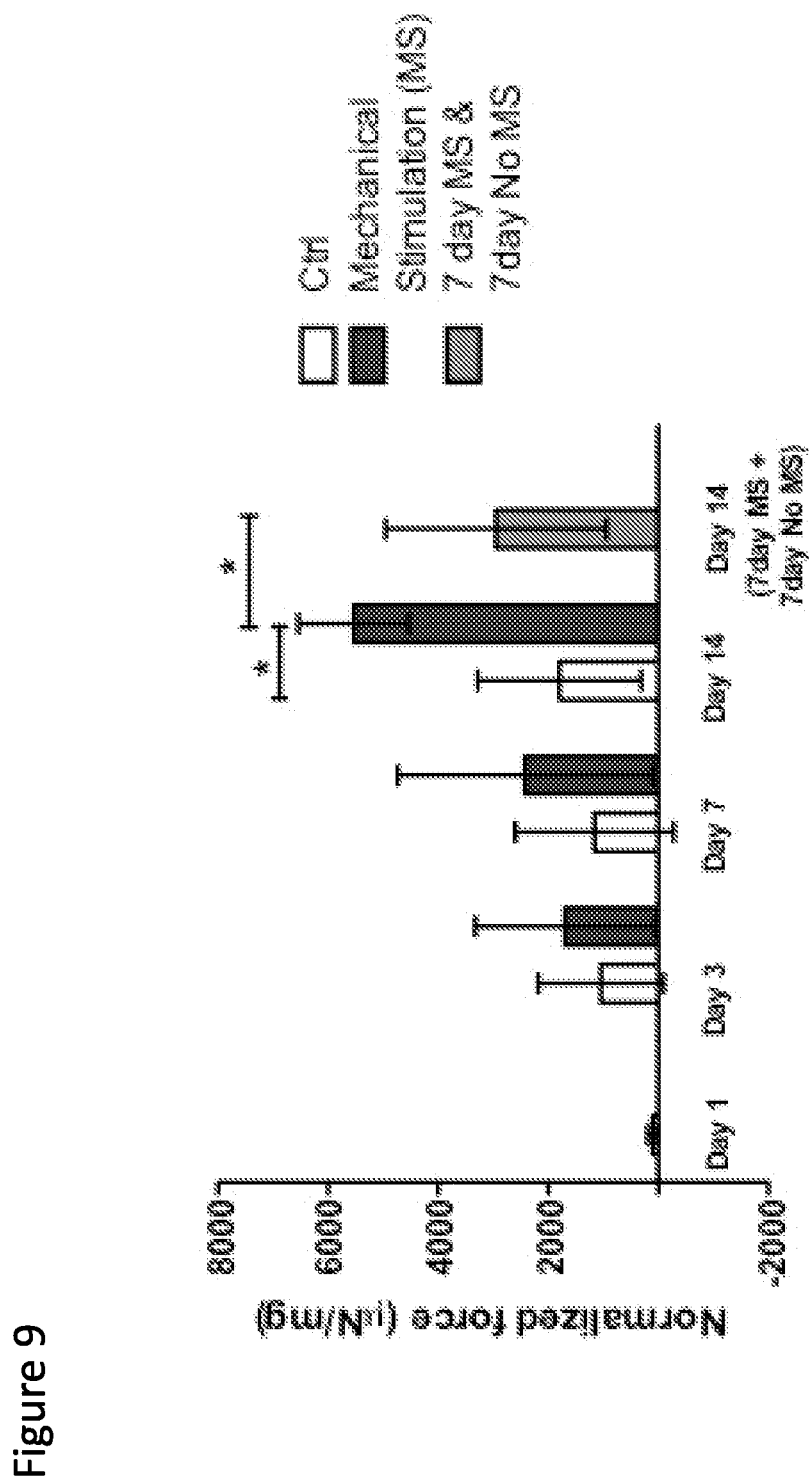

FIG. 9 depicts recovery of muscle tetanic force in response to pressure cuff-mediated mechanical stimulation. The average contractile force of injured tibialis anterior muscle was measured 24 hours after ischemia surgery (Day 1) without any treatment or after 3, 7, and 14 days with and without mechanical stimulation. Control (Ctrl) indicates non-treated control group. Data were compared using ANOVA with Bonferroni's post-hoc test (N=5-9, *p<0.05).

Figure 10:
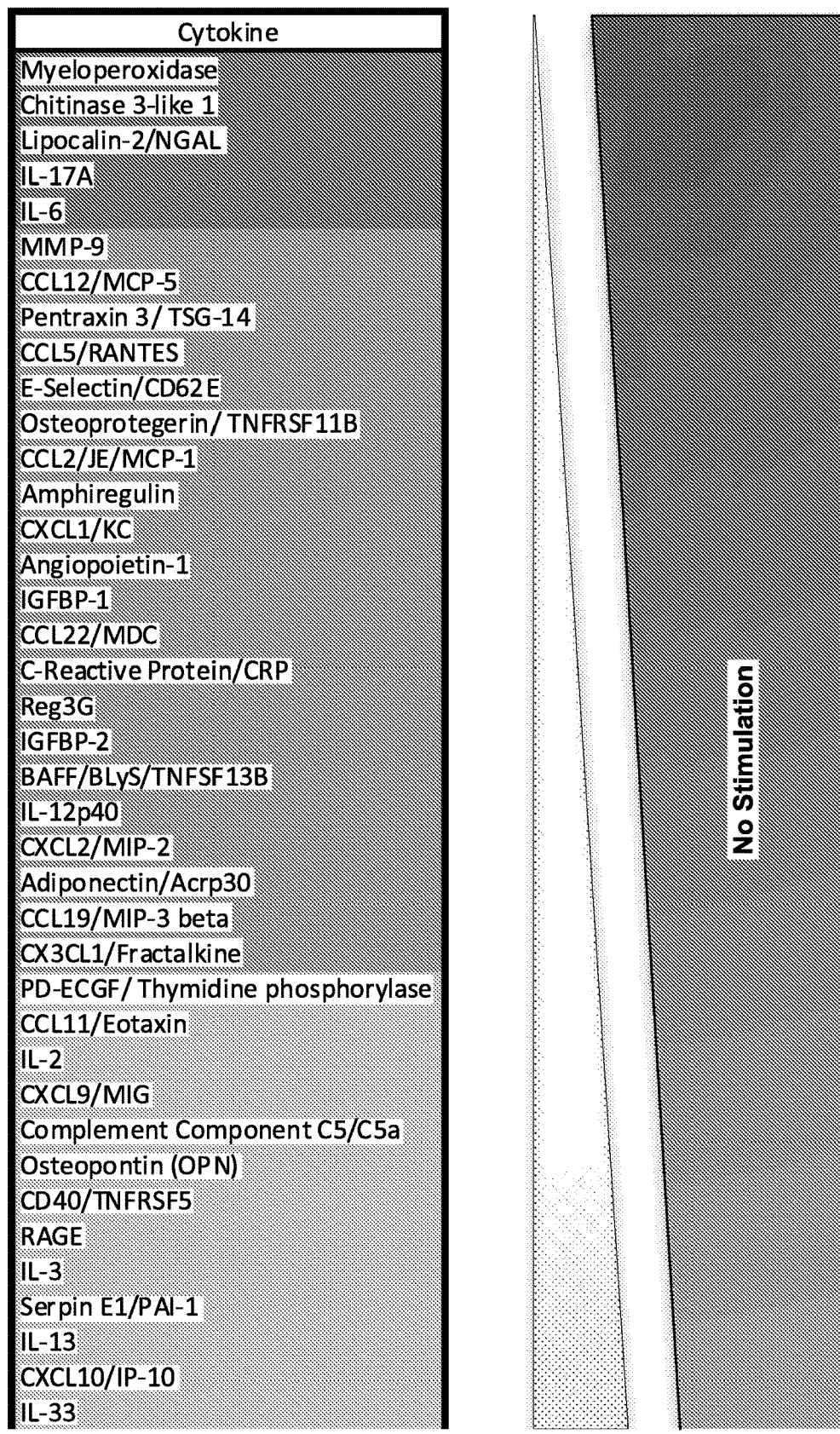
Figure 10:
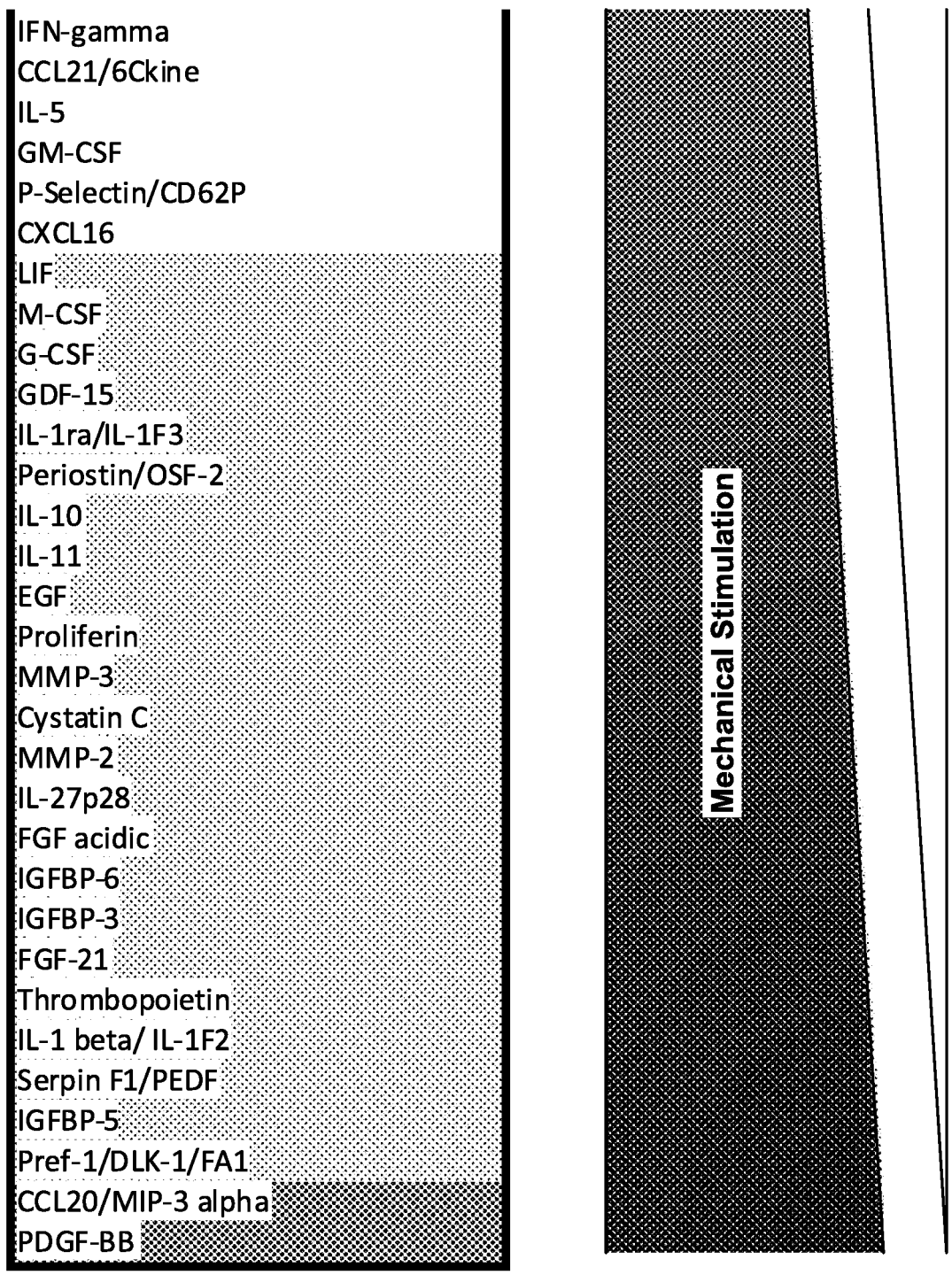

FIG. 10 depicts changes in cytokine levels from the injured muscle by mechanical stimulation. Levels of listed cytokines were screened on the injured muscle treated with and without mechanical stimulation for 7 days after ischemic injury. The intensity of color indicates the degree of difference.

Figure 11:
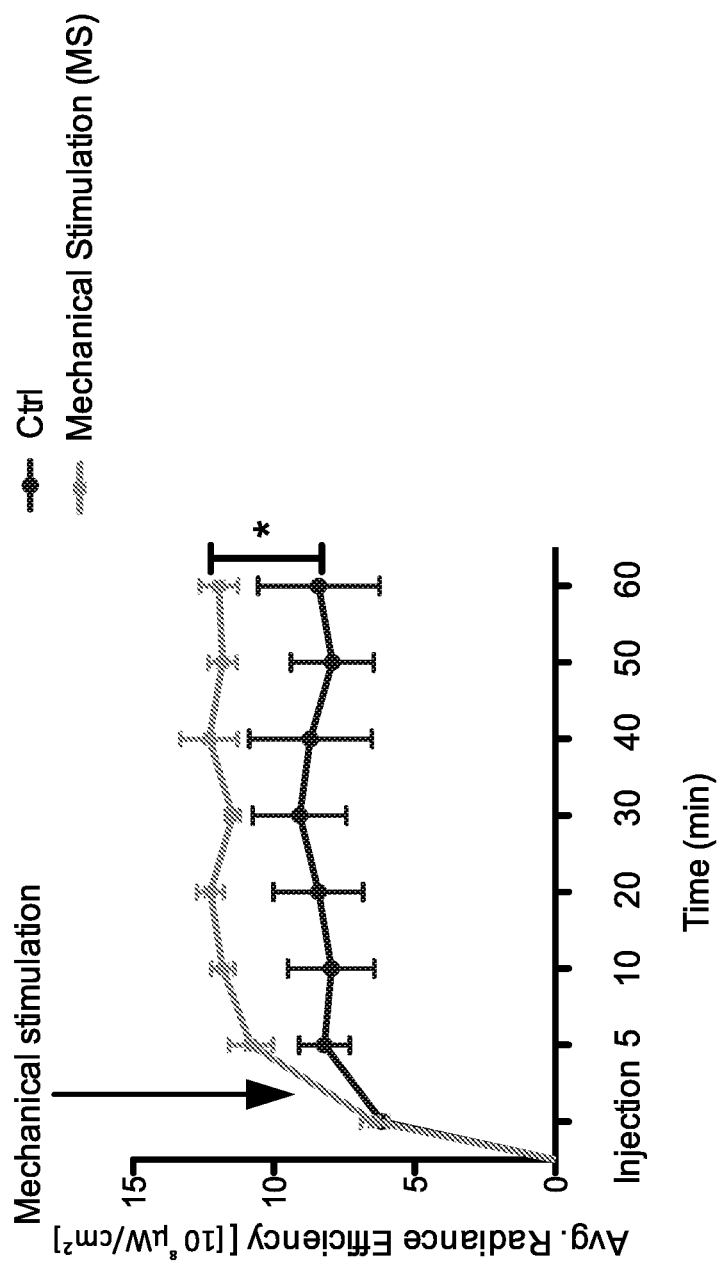

FIG. 11 depicts kinetics of fluorescent intensities from intramuscularly injected dextran in response to mechanical stimulation. Changes in signals of fluorescently labeled dextran injected into tibialis anterior muscle were measured post-injection and post-mechanical stimulation (from 5 to 60 minutes). Control (ctrl) indicates non-treated control group. Data were compared using Student's t-test, (N=3, *p<0.05).

DETAILED DESCRIPTION OF THE INVENTION

The present invention is based, at least in part, on the discovery that devices with a capacity to apply cyclic compression forces such as biphasic ferrogels and pressure cuffs can be used to mechanically stimulate and regenerate injured tissue, e.g., muscle tissue, without the use of growth factors or cells. In particular, both magnetic actuation of biphasic ferrogel scaffolds implanted at the site of muscle injury and external actuation of compression device surrounding the site of muscle injury resulted in uniform cyclic compressions that led to reduced fibrous capsule formation around the implant, as well as reduced fibrosis and inflammation in the injured muscle. Furthermore, ferrogel-driven and pressure cuff-driven mechanical compressions led to enhanced muscle regeneration and an approximately 3- and 2.2-fold increase in maximum contractile force of the treated muscle, respectively.

Accordingly, the present invention provides methods and compositions for promoting regeneration of a tissue in a subject in need thereof. Other embodiments of the invention include methods relating to preventing or reducing inflammation of a tissue, preventing or reducing fibrosis of a tissue, increasing a mass of a tissue, enhancing a function of a tissue, increasing a level of oxygen available to a tissue, increasing a rate of metabolic waste product removal from a tissue and increasing blood perfusion of a tissue in a subject in need thereof. In a further embodiment, the invention includes methods for treating a severe muscle tissue damage in a subject in need thereof.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "cyclic mechanical compression" refers to the repeated cyclic application of pressure followed by a release of that pressure that, in turn, results in a compression and a decompression of the target tissue.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration, the progression or severity of a condition associated with such a disease or disorder. In one embodiment, the symptoms of a disease or disorder are alleviated by at least 5%, at least 10%, at least 20%, at least 30%, at least 40%, or at least 50%.

As used herein, the term "polymer" is intended to include both oligomeric and polymeric species, i.e., compounds which include two or more monomeric units, which may be a homopolymer or a copolymer. The term "homopolymer" is a polymer incorporating a single species of monomer units. The term "copolymer" is a polymer constructed from two or more chemically distinct species of monomer units in the same polymer chain. A "block copolymer" is a polymer which incorporates two or more segments of two or more distinct species of homopolymers or copolymers.

As used herein, the term "swelling agent" refers to those compounds or substances which affect at least a degree of swelling. Typically, swelling agents is an aqueous solution or organic solvent, however swelling agent can also be a gas. In some embodiments, swelling agent is water or a physiological solution, e.g. phosphate buffer saline, or growth media.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but this term is not limited to these examples. Mammals other than humans can be advantageously used as subjects that represent animal models of muscle injury or damage, or other related pathologies. In addition, the methods described herein can be used to treat domesticated animals and/or pets. A subject can be male or female. A subject can be one who has been previously diagnosed with or identified as suffering from or having tissue injury or damage, e.g., muscle tissue injury or damage, or having one or more complications related to such tissue injury or damage. Optionally, such subjects have not already undergone treatment for the tissue injury damage.

As used herein the term "surrounding a site of tissue damage" refers to, at least, encircling the site of tissue damage, but does not require that the site of tissue damage be surrounded on all sides. For example, it does not require that the tissue damage be surrounded over all of the polar angle of inclination from 0 to 180 degrees and all of the azimuthal angle of 0 to 360 degrees extending outward from the center of the site of tissue damage. In one embodiment, the term includes surrounding the tissue damage over all sides, for example, over all of the polar angle of inclination from 0 to 180 degrees and all of the azimuthal angle of 0 to 360 degrees extending outward from the center of the site of tissue damage.

II. Methods of the Invention

In one aspect, the invention provides methods for promoting regeneration of a tissue, e.g., muscle tissue, in a subject in need thereof. The methods of the present invention include contacting the tissue, e.g., muscle tissue, with a composition suitable for applying cyclic mechanical compressions, and applying cyclic mechanical compression to the tissue, e.g., muscle tissue, thereby promoting regeneration of the tissue, e.g., muscle tissue.

As used herein, the term "contacting" (e.g., contacting a tissue, e.g., a muscle tissue, or a plurality of tissues with a composition) is intended to include any form of interaction (e.g., direct or indirect interaction) of a composition and a tissue or a plurality of tissues. The term contacting includes incubating a composition and a tissue or a plurality of tissues together, e.g., injecting or implanting the composition to a tissue or a plurality of tissues in a subject or placing the composition on a tissue or a plurality of tissues together in a subject, e.g., by configuring the composition to be disposed externally to the body and surrounding a tissue or a plurality of tissues from at least a portion of a body part (e.g., a limb, a spine, a neck, a waist, a shoulder, a knee, a joint, an ankle, a calf, a thigh, a foot, a hand, a wrist, an arm, a should or an axilla), or by configuring the composition to be disposed, at least partially, internally within the body and to, at least partially, surround a tissue or a plurality of tissues from a body part (e.g. an esophagus, a urethral sphincter or an anal sphincter).

The term "cyclic mechanical compression" refers to the repeated cyclic application of pressure followed by a release of that pressure which, in turn, results in a compression and a decompression of the target tissue, e.g., a muscle tissue, a bone tissue, or an endothelial tissue.

In some embodiments, the target tissue is intact. In other embodiments, the target tissue is damaged. In some embodiments, the site of tissue damage is on or in a limb, a spine, a neck, a waist, a shoulder, a knee, or a joint of a subject. In some embodiments, the limb is a lower limb of the subject and the site of tissue damage is on or in an ankle, a calf, a thigh or a foot. In other embodiments, the limb is a upper limb of the subject and the site of tissue damage is on or in a hand, a wrist, an arm, a shoulder or an axilla. In some embodiments, the site of tissue damage is within an esophagus of a subject. In other embodiments, the site of tissue damage is within an urethral or anal sphincter of a subject.

In some embodiments, the tissue, e.g., muscle tissue, is contacted with the composition suitable for applying cyclic mechanical compression at the site of tissue damage after the damage has occurred. In some embodiments, cyclic mechanical compressions are applied to the site of tissue damage immediately after the damage has occurred. For example, cyclic mechanical compressions are applied to the site of tissue damage within less than 5, 10, 20, 30, 40, 50, 60 minutes after the damage has occurred. In other embodiments, cyclic mechanical compressions are applied to the site of tissue damage at least 1, 2, 3, 4, 5, 7, 8, 9, 10, 12 or 24 hours after the damage has occurred. In some embodiments, cyclic mechanical compressions are applied to the site of tissue damage at least 1, 2, 3, 4, 5, 6, 7, 8, 9, 10 days or at least 1, 2, 3, 4, 5, 6, 7, 8, 9, 10 11, 12, 24, 48 or 60 months after the damage has occurred. In other embodiments, cyclic mechanical compressions are applied to the site of tissue damage at least 1, 2, 3, 4, 5, 6 years after the damage has occurred.

In some embodiments, cyclic mechanical compressions, generated by the composition suitable for applying cyclic mechanical compression, are applied to the tissue, e.g., a muscle tissue, at the site of tissue damage over a period of time, for example, for at least 1, 2, 3, 4, 5, 6, 7, 8, 9, 10, 11, 12, 24, 36, 48, 60, 72, 84, 96 or 120 hours. In other embodiments, cyclic mechanical compressions are applied to the site of tissue damage for about 1 to 30 days, about 1 to 50 days, about 1 to 100 days, about 1 to 200 days or about 1 to 300 days. In certain embodiments, the cyclic mechanical compressions are applied to the site of tissue damage until the tissue damage has been recovered.

In some embodiments, cyclic mechanical compressions are applied with a peak pressure of at least 0.1, 1, 2, 3, 4, 5, 6, 7, 8, 9, 10, 20, 30, 40, 50, 60, 70, 80, 90, 100, 200, 300, 400, 500, 600, 700, 800, 900 or 1000 kPa. In other embodiments, cyclic mechanical compressions are applied with a peak pressure of about 0.1 kPa to 1000 kPa, about 1-10 kPa, about 1-20 kPa, about 1-30 kPa, about 1-50 kPa, about 1-100 kPa, about 1-1000 kPa, about 10-100 kPa, about 10-200 kPa, about 10-300 kPa, about 10-500 kPa, about 10-1000 kPa, about 100-1000 kPa, about 200-1000 kPa, about 300-1000 kPa, about 400-1000 kPa, about 500-1000 kPa, about 600-1000 kPa, about 700-1000 kPa, about 800-1000 kPa, or about 900-1000 kPa.

In some embodiments, cyclic mechanical compressions are applied at least once daily. In other embodiments, cyclic mechanical compressions are applied at least three times daily.

Cyclic mechanical compressions applied by the composition suitable for the methods of the present invention can be generated by any known methods in the art, for example, by an electromagnetic signal. The electromagnetic signal, which causes the composition to apply cyclic mechanical compression to the tissue, can be produced by an electronic signal generator. The term "electronic signal generator", as used herein, may include an electromagnet or electrically-polarizable element, or at least one permanent magnet. In some embodiments, the electromagnetic signal can be produced at least in part according to a pre-programmed pattern. The electromagnetic signal may have a defined magnetic field strength or spatial orientation, or a defined electric field strength or spatial orientation. In some embodiments, the electromagnetic signal is generated by application of a magnetic field. In other embodiments, the electromagnetic signal has a defined magnetic field strength.

As used herein, the term "magnetic field" refers to magnetic influences which create a local magnetic flux that flows through the composition and can refer to field amplitude, squared-amplitude, or time-averaged squared-amplitude. It is to be understood that magnetic field can be a direct-current (DC) magnetic field or alternating-current (AC) magnetic field. Magnetic field strength can range from about 0.001 Tesla to about 1 Tesla. In some embodiments, magnetic field strength is in the range from about 0.01 Tesla to about 1 Tesla. In some other embodiments, magnetic field strength is in the range from about 0.1 Tesla to about 1 Tesla. In other embodiments, the magnetic field strength is about 0.5 Tesla.

Cyclic mechanical compressions applied by the composition suitable for the methods of the present invention can also be generated by a device, for example, a compression device comprising a surrounding member configured to encircle a body part, and a controller configured to generate cyclic mechanical compression in the surrounding member.

As used herein, a "controller" is a device or system configured to generate cyclic mechanical compressions and to control properties of the cyclic mechanical compressions, such as, the frequency, the amplitude and/or the duration of the cyclic mechanical compressions being generated. In some embodiments, the controller includes a microcontroller that controls the properties of the cyclic mechanical compressions. In some embodiments, the controller includes storage for holding machine readable instructions, measurements of pressure from a pressure sensor, or other information. In some embodiments, microcontroller includes storage for holding machine readable instructions, measurements of pressure from a pressure sensor, or other information. In some embodiments, the controller includes additional storage that is not included in the microcontroller, but is accessible to the microcontroller for holding machine readable instructions, measurements of pressure from a pressure sensor, or other information.

Existing treatments for tissue regeneration have mainly focused on the delivery of biologics, e.g., relying on the use of cell and growth factor-based approaches. The methods of the present invention, however, are based, at least in part, on the surprising discovery that mechanical stimulation alone, e.g., cyclic mechanical compressions, on the target tissue is sufficient to enhance tissue repair. For example, the development of a composition that can apply cyclic mechanical compressions to a damaged tissue, e.g., a muscle tissue, without the use of growth factors or cells, can be used to mechanically stimulate and regenerate damaged tissue, representing a novel therapeutic strategy for treatment of tissue injuries.

The term "tissue regeneration", as used herein, encompasses both regeneration of tissue with recourse to exactly the type of tissue to be regenerated, in the sense of an increase in the mass of the tissue, as well as the production of new tissue starting from a different type of tissue or cell than that to be produced. For example, the term "muscle regeneration" refers to the process by which new muscle fibers form from muscle progenitor cells. The growth of muscle may occur by the increase in the fiber size and/or by increasing the number of fibers. The growth of muscle may be measured by an increase in weight, an increase in protein content, an increase in the number of muscle fibers, or an increase in muscle fiber diameter. An increase in growth of a muscle fiber can be defined as an increase in the diameter where the diameter is defined as the minor axis of ellipsis of the cross section.

The tissue, e.g., muscle tissue, regenerated based on the methods of the present invention is functional. The functional quality of the regenerated muscle tissue can be measured by any methods known in the art. For example, as demonstrated in Example 6 of the present invention, the function of the regenerated muscle tissue can be measured by the contractile force of each regenerated muscle. Peak tetanic force can be determined as the difference between the maximum force during contraction and the baseline level. An increase in the maximum contractile force of muscle tissue upon treatment with cyclic mechanical compressions indicates that the regenerated muscle tissue is functional. The increase in the maximum force of the regenerated muscle tissue can be, for example, at least 0.5-fold, 1-fold, 1.5-fold, 2-fold, 2.5-fold, 3-fold, 3.5-fold, 4-fold, 4.5-fold, 5-fold, 10-fold, 20-fold, 30-fold or 50-fold.

The methods of the present invention are suitable for promoting regeneration of any type of tissue, such as external epithelial tissue, internal epithelial tissue, endothelial tissue or mesenchymal tissue. Examples of tissue that can be regenerated based on the methods of the present invention may include, but not limited to, heart tissue, blood vessel tissue, skin tissue, muscle tissue, bone tissue, cartilage tissue, connective tissue, tendon tissue, and ligament tissue.

In some embodiments, the methods of the present invention are suitable for promoting regeneration of a muscle tissue. The phrase "muscle tissue", as used herein, encompasses any mammalian muscle tissue. In some embodiments, the muscle tissue is a human muscle tissue. In other embodiments, the muscle tissue is a muscle tissue from a domesticated animal, a pet or a game animal, for example, a dog muscle tissue, a horse muscle tissue, a cow muscle tissue, or a rabbit mouse tissue. In some embodiments, the muscle tissue is selected from the group consisting of a smooth muscle tissue, a skeletal muscle tissue and a cardiac muscle tissue. Skeletal muscle tissue is under voluntary control. The muscle fibers are syncytial and contain myofibrils, tandem arrays of sarcomeres. Smooth muscle tissue is made up from long tapering cells, generally involuntary and differs from striated muscle in the much higher actin/myosin ratio, the absence of conspicuous sarcomeres and the ability to contract to a much smaller fraction of its resting length. Smooth muscle cells are found particularly in blood vessel walls, surrounding the intestine and in the uterus. Cardiac muscle tissue is a striated but involuntary tissue responsible for the pumping activity of the vertebrate heart. The individual cardiac muscle cells are not fused together into multinucleate structures as they are in striated muscle tissue. As used herein, the phrases "cardiac muscle tissue" and "myocardium tissue" are interchangeable.

In some embodiments, the muscle tissue is damaged. As used herein, the terms "damaged muscle tissue" or "muscle tissue damage" refer to a muscle tissue, such as a skeletal or cardiac muscle that has been altered for instance by a physical injury or accident, disease, infection, over-use, loss of blood circulation, or by genetic or environmental factors such as cryo-damage. As used herein, the term "cryo-damage" refers to damage to tissues, cells, or other biological substrates as a result of exposure to cold. In other embodiments, a damaged muscle tissue is a dystrophic muscle or an aging muscle.

In some embodiments, the muscle tissue damage is a severe muscle tissue damage. A severe muscle tissue damage refers to a muscle mass loss or injury of greater than about 20%, e.g., about greater than 25%, 30%, 35%, 40%, 45% or 50%. Severe muscle tissue injures resulting in a muscle mass loss or injury of greater than about 20% can lead to extensive fibrosis and loss of muscle function.

In some embodiments, muscle tissue damage is induced by mechanical injury, such as acute and chronic strains. In other embodiments, muscle tissue damage is induced by exercise or muscle laceration, e.g., post-exercise muscular cramp. In some embodiments, muscle tissue damage is induced by loss of muscle tissue due to disease such as myopathy. Without limitation, myopathy can be a congenital myopathy or an acquired myopathy. Exemplary myopathies include, but are not limited to, dystrophies, myotonia (neuromytonia), congenital myopathies (e.g., nemaline myopathy, multi/minicore myopathy, centronuclear myopathy (or myotubular myopathy)), inflammatory myopathies, metabolic myopathies (e.g., glycogen storage disease and lipid storage disorder), dermatomyositis, polymyositis inclusion body myositis, myositis ossificans, rhabdomyolysis and myoglobinuirias.

In some embodiments, myopathy is a dystrophy selected from the group consisting of muscular dystrophy, Duchenne muscular dystrophy, Becker's muscular dystrophy, reflex sympathetic dystrophy, detinal dystrophy, conal dystrophy, myotonic dystrophy, corneal dystrophy, and any combinations thereof.

In some embodiments, muscle tissue damage is induced by muscle hypertrophy. In other embodiments, muscle tissue damage is induced by muscle atrophy or wasting, e.g., muscle wasting from post-surgery bed rest. In some embodiments, muscle tissue damage is induced by genetic disorders such as, but not limited to muscular dystrophies. In other embodiments, muscle tissue damage is induced by chronic disorders such as, but not limited to AIDS, cancer, chronic heart failure, and kidney disease. In some embodiments, muscle tissue damage is induced by diseases related to aging.

In some embodiments, muscle tissue damage is induced by diseases related to inflammation of connective tissues surrounding muscle, for example, fasciitis. As used herein, the term "fasciitis" refers to an inflammation of fascia, which is the connective tissue surrounding muscles, blood vessels and nerves. Exemplary fasciitis diseases include, but not limited to, plantar fasciitis which is one of the most common causes of pain in heel and the bottom of the foot; eosinophilic fasciitis which is a disorder that results in pain and inflammation in arms and legs, and necrotizing fasciitis which involves infection of deeper layers of skin and subcutaneous tissues.

In some embodiments, the muscle tissue damage is induced by toxin. In other embodiments, the muscle tissue damage is induced by ischemia. In some embodiments, the muscle tissue damage is induced by a combination of toxin and ischemia. In other embodiments, the muscle tissue damage is induced by hind limb ischemia. In some embodiments, the muscle tissue damage is induced by trauma.

Exemplary symptoms of muscle damage include, but are not limited to, swelling, bruising or redness, open cuts as a consequence of an injury, pain at rest, pain when specific muscle or the joint in relation to that muscle is used, weakness of the muscle or tendons, and an inability to use the muscle at all.

The principle of using mechanical stimulation, e.g., cyclic mechanical compressions, to enhance tissue regeneration can be applied to any type of tissue. In some embodiments, the methods of the present invention are suitable for promoting regeneration of an endothelial tissue. Endothelial tissue or cells make up the structure of blood vessels. Endothelial cells are involved in many aspects of vascular biology such as angiogenesis, e.g., formation of new blood vessels, repair of damaged or disease organs, and control of blood pressure through vasoconstriction and vasodilation. Accordingly, regeneration of endothelial cells is critical for angiogenesis and organ repair.

In other embodiments, the methods of the present invention are suitable for promoting regeneration of a bone tissue. Bone tissue regeneration is often required in conditions such as skeletal reconstruction of large bone defects created by trauma, infection, tumor resection and skeletal abnormalities, or cases in which regenerative process is comprised, including avascular necrosis and osteoporosis.

In one aspect, the invention provides a method for increasing a mass of a tissue in a subject in need thereof. An increase in the mass of a tissue represents a marker for successful tissue regeneration. The method of the present invention comprises contacting the tissue with a composition suitable for applying cyclic mechanical compressions, and applying cyclic mechanical compression to the tissue, thereby increasing the mass of the tissue.

The methods of the present invention are suitable for increasing the mass of any type of tissue, such as external epithelial tissue, internal epithelial tissue, endothelial tissue or mesenchymal tissue. Examples of tissue that can be regenerated based on the methods of the present invention may include, but not limited to, heart tissue, blood vessel tissue, skin tissue, muscle tissue, bone tissue, cartilage tissue, connective tissue, tendon tissue, and ligament tissue.

In some embodiments, the methods of the present invention are suitable for increasing the mass of a muscle tissue. The mass of a muscle tissue can be enhanced by increasing the mitogenesis, myogenesis, differentiation, or survival of muscle cells in a subject, for example, a mammal, i.e., a human. The methods of the present invention are also suitable to slow or halt net muscle loss or to increase the amount or quality of muscle present in a subject.

The term "muscle cell", as used herein, refers to any cell which contributes to muscle tissue. Myoblasts, satellite cells, myotubes, and myofibril tissues are all included in the term "muscle cells" and may all be regenerated using the methods of the invention.

Mitogenesis, as used herein, refers to any cell division which results in the production of new muscle cells in the subject. Mitogenesis may be induced in muscle cells of skeletal muscle, smooth muscle or cardiac muscle. Mitogenesis in vitro can be measured by any methods known in the art. For example, mitogenesis can be assayed by exposing cells to a labeling agent for a time equivalent to two doubling times, and calculating the mitotic index. The mitotic index is the fraction of cells in the culture which have labeled nuclei when grown in the presence of a tracer, i.e., BrdU, which only is incorporated during S phase of the cell cycle, and the doubling time is defined as the average time required for the number of cells in the culture to increase by a factor of two. Mitogenesis is defined by an increase in mitotic index relative to untreated cells of at least 50%, e.g., 60%, 70%, 80%, 90%, 100%, 150%, 200%, 250% or 300%.

Myogenesis, as used herein, refers to any fusion of myoblasts to yield myotubes. An effect on myogenesis is defined as an increase in the fusion of myoblasts and the enablement of the muscle differentiation program, which is characterized as a fusion index in vitro. The fusion index is defined as the fraction of nuclei present in multinucleated cells in the culture relative to the total number of nuclei present in the culture. Myogenesis may also be determined by assaying the number of centrally located nuclei per area in myotubes, as demonstrated in Example 3 of the present invention, or by measurement of the levels of muscle specific protein by Western analysis.

The survival of muscle fibers, as used herein, refers to the prevention of loss of muscle fibers as evidenced by necrosis or apoptosis or the prevention of other mechanisms of muscle fiber loss. Survival as used herein indicates an decrease in the rate of cell death of at least 10%, 20%, 30%, 40%, 50%, 60%, 70%, 80%, 90%, 100% relative to an untreated control. The rate of survival may be measured by counting cells stainable with a dye specific for dead cells (such as propidium iodide) in culture when the cells are a couple days post-differentiation.

In another aspect, the invention provides methods for increasing a function of a tissue in a subject in need thereof. These methods include contacting the tissue with a composition suitable for applying cyclic mechanical compressions, and applying cyclic mechanical compression to the tissue, thereby increasing the function of the tissue in the subject.

The functional quality of the regenerated tissue, e.g., a muscle tissue, can be measured by any methods known in the art. For example, as demonstrated in Example 6 of the present invention, the function of the regenerated muscle tissue can be measured by the contractile force of each regenerated muscle. Peak tetanic force can be determined as the difference between the maximum force during contraction and the baseline level. An increase in the maximum contractile force of muscle tissue upon treatment with cyclic mechanical compressions indicates that the regenerated muscle tissue is functional. The increase in the maximum force of the regenerated muscle tissue can be, for example, at least 0.5-fold, 1-fold, 1.5-fold, 2-fold, 2.5-fold, 3-fold, 3.5-fold, 4-fold, 4.5-fold, 5-fold, 10-fold, 20-fold, 30-fold or 50-fold.

In yet another aspect, the invention provides methods for preventing or reducing inflammation of a tissue in a subject in need thereof. These methods include contacting the tissue with a composition suitable for applying cyclic mechanical compressions, and applying cyclic mechanical compression to the tissue, thereby preventing or reducing inflammation of the tissue.

The term "inflammation" refers to a part of the complex biological response of body tissues to harmful stimuli, such as pathogens, damaged cells, irritants, ischemic and toxic assaults. The purpose of inflammation is to eliminate the initial cause of cell injury, clear out necrotic cells and tissues damaged from the original insult and the inflammatory process, and to initiate tissue repair. Inflammation can be classified as either acute or chronic. Acute inflammation is the initial response of the body to harmful stimuli and is achieved by the increased movement of plasma and leukocytes from the blood into the injured tissues. Chronic inflammation leads to a progressive shift in the type of cells present at the site of inflammation and is characterized by simultaneous destruction and healing of the tissue from the inflammatory process. As a result, the inflammatory response represents a two-sided sword: beneficial in terms of the repair process to injury; detrimental when proceeding in an uncontrolled manner, which then leads to progressive fibrosis with a loss of function. Thus, controlling excessive inflammation would be of great potential therapeutic benefit for inhibiting progressive fibrosis during tissue injury.

Fibrosis, as used herein, refers to a process of wound healing and repair that is activated in response to injury and is associated with chronic inflammatory diseases. A key event leading to fibrous capsule formation is the adhesion of immune cells, such as macrophages, to the site of injury, and these cells secrete proteins that modulate fibrosis leading to the proliferation and activation of fibroblasts, which results in an excessive deposition of extracellular matrix in the surrounding tissue and impairs the architecture and function of the underlying tissue.

Inflammation can be characterized by signs or manifestations comprising redness, swelling, heat, pain, and the loss of function of the involved tissue. The presence of inflammation in the involved tissue indicates the presence of injury or disease, while the amount of inflammation in the injured, damaged or deformed tissue is directly proportional to the amount of damage or disease in that tissue and is inversely proportional to the degree of healing in the same tissue. Various methods and equipment have been developed for assessing the presence or absence of inflammation in tissues. Such methods and equipment include performing a physical examination of the involved tissue; blood tests, such as erythrocyte sedimentation rate or C-reactive protein level; radiographic tests, such as plain X-rays or magnetic resonance imaging (MRI); and research procedures, such as thermography.

Additional methods for monitoring the presence or absence of inflammation in tissues include examining the level of tissue scarring and fibrosis using histologic sections. For example, the extent of tissue fibrosis can be assessed by visualizing picosirius red stained collagen I and III under polarized light. Alternatively, the extent of tissue fibrosis can be determined by quantification of inflammatory infiltrate at the site of injury.

Compositions suitable for use in the methods of the present invention are suitable for injection, implantation or disposing internally within the body, e.g., at the site of tissue damage. In some embodiments, the compositions are configured to surround or encircle a body part or at least a portion of a body part (e.g., an esophagus, a urethral sphincter, or an anal sphincter). In other embodiments, the compositions suitable for use in the methods of the present invention are implanted or disposed internally within the body, at a site of tissue damage upon major surgery to assist tissue regeneration or to treat tissue injury.

Compositions suitable for use in the methods of the present invention are also suitable to be disposed externally to the body and surround at least a portion of a body part (e.g., a limb, a spine, a neck, a waist, a shoulder, a knee, a joint, an ankle, a calf, a thigh, a foot, a hand, a wrist, an arm, a shoulder, or an axilla).

Current clinical devices are often plagued by the formation of thickened tissue capsules upon implantation at the site of interaction between the mechanical components and the body tissues. The ability to inhibit fibrous capsule formation with cyclic mechanical compressions has a great potential utility for implantable drug delivery devices and sensors that require unobstructed diffusion around the implant for proper function. As demonstrated in Example 4 of the present invention, application of cyclic mechanical compressions at the injured tissue resulted in a reduction in fibrous capsule thickness and a decrease amount of inflammatory cells at the site of implant, thus alleviating the overall inflammation in the target tissue.

Accordingly, in one aspect, the invention provides methods for preventing or reducing fibrosis of a tissue in a subject, e.g., a tissue at a site of implantation in a subject. The methods of the present invention include contacting the tissue with a composition suitable for applying cyclic mechanical compressions, and applying cyclic mechanical compression to the tissue, thereby preventing or reducing fibrosis of a tissue in the subject.

The principle of using mechanical stimulation, e.g., cyclic mechanical compressions, to enhance tissue regeneration or to reduce formation of scarring or fibrosis can be applied to any type of tissue, such as external epithelial tissue, internal epithelial tissue, endothelial tissue or mesenchymal tissue. Examples of suitable tissue for this method include, but not limited to, heart tissue, blood vessels, skin tissue, muscle tissue, bone tissue, cartilage tissue, connective tissue, tendon tissue, and ligament tissue.

In some embodiments, formation of fibrous capsule at the site of tissue damage is reduced. In other embodiments, thickness of fibrous capsule at the site of tissue damage is reduced. In yet another embodiment, inflammatory cell removal at the site of tissue damage is accelerated.

The direct application of cyclic mechanical compressions to the target tissue may provide an additional convection-based benefit. For example, enhanced fluid transportation around the site of implant may increase the blood perfusion as well as the transport of oxygen, nutrients, fluids to the site of injury. In addition, the direct stimulation of target tissue may accelerate immune cell and/or metabolic waste removal from the site of the injury, which are all vital components of tissue health and repair. Invading inflammatory cells near the site of injury may be expelled upon stimulation, due to fluid convection resulting from the cyclic mechanical compressions, leading to an overall diminished cell presence within the site of injury.

Thus, in one aspect, the invention provides methods for increasing a level of oxygen available to a tissue in a subject in need thereof. These method include contacting the tissue with a composition suitable for applying cyclic mechanical compressions, and applying cyclic mechanical compression to the tissue, thereby increasing the level of oxygen available to the tissue.

The oxygen level generated by the issue may be increased by increasing blood flow to the tissue. Alternatively, the oxygen level is increased by enhanced intramuscular convection driven by cyclic mechanical compressions of the tissue.

In another aspect, the invention provides methods for increasing the rate of metabolic waste product removal from a tissue in a subject in need thereof. These method include contacting the tissue with a composition suitable for applying cyclic mechanical compressions, and applying cyclic mechanical compressions to the tissue, thereby increasing the rate of metabolic waste product removal from the tissue.

In some embodiments, the rate of metabolic waste product removal is increased by enhanced fluid transportation driven by cyclic mechanical compressions around the site of implantation within the tissue.

In yet another aspect, the invention provides methods of increasing blood perfusion to a tissue in a subject in need thereof. These methods include contacting the tissue with a composition suitable for applying cyclic mechanical compressions, and applying cyclic mechanical compression to the tissue, thereby increasing blood perfusion to the tissue.

In one aspect, the invention provides methods for promoting regeneration of a muscle tissue in a subject suffering from muscle damage induced by a myotoxin and ischemia. These method include contacting the muscle tissue with a composition suitable for applying cyclic mechanical compressions, and applying cyclic mechanical compression to the muscle tissue, thereby promoting regeneration of the muscle tissue.

In another aspect, the invention provides methods of treating a severe muscle tissue damage in a subject in need thereof. These methods include contacting the muscle tissue with a composition suitable for applying cyclic mechanical compressions, and applying cyclic mechanical compressions to the muscle tissue, thereby treating the severe muscle tissue damage in the subject.

The term "treating" used herein encompasses the complete range of therapeutically positive effects of contacting a composition suitable for applying cyclic mechanical compressions to a tissue, e.g., a muscle tissue, including improving the tissue function, providing mechanical support and promoting tissue healing and repair processes. The term treating further includes reduction of, alleviation of, and relief of symptoms of diseases or disorders associated with an injured or damaged tissue, e.g., a damaged muscle tissue. In addition, the term treating includes prevention or postponement of development of symptoms of diseases or disorders associated with an injured or damaged tissue, e.g., a damaged muscle tissue.

The methods of the present invention are applicable in a variety of conditions. Exemplary diseases or disorders associated with an injured or damaged tissue, e.g., a damaged muscle tissue, may include, but not limited to, muscular dystrophy, Duchenne muscular dystrophy, Becker's muscular dystrophy, reflex sympathetic dystrophy, detinal dystrophy, conal dystrophy, myotonic dystrophy, corneal dystrophy, fasciitis, plantar fasciitis, eosinophilic fasciitis, necrotizing fasciitis, post-exercise muscular cramp, pain or inflammation from cervical neck, mechanical injury such as acute and chronic strains, myopathy, dystrophies, myotonia (neuromytonia), congenital myopathies (e.g., nemaline myopathy, multi/minicore myopathy, centronuclear myopathy (or myotubular myopathy)), inflammatory myopathies, metabolic myopathies (e.g., glycogen storage disease and lipid storage disorder), dermatomyositis, polymyositis inclusion body myositis, myositis ossificans, rhabdomyolysis and myoglobinuirias, muscle hypertrophy, muscle atrophy or wasting, e.g., muscle wasting from post-surgery bed rest, muscle fatigue, or any diseases or disorders resulting from a physical injury or accident, trauma, infection, inflammation, loss of blood circulation, or by genetic or environmental factors.

III. Compositions Suitable for Use in the Methods of the Invention

Compositions suitable for use in the methods of the present invention are capable of applying cyclic mechanical compressions to a site of tissue damage, e.g., muscle tissue damage. Cyclic mechanical compressions applied by the compositions suitable for use in the methods of the present invention can be generated by any known methods in the art. In some embodiment, the cyclic mechanical compressions applied by the compositions are generated by an electromagnetic signal. In other embodiments, the cyclic mechanical compressions are generated by pneumatic actuation or hydraulic actuation. In yet another embodiment, the cyclic mechanical compressions applied by the compositions are generated by a controller.

A. Magnetic Material-Based Compression Compositions

A magnetic material-based compression composition suitable for use in the methods of the present invention comprises a matrix material and a magnetic material distributed therethrough, wherein the composition comprises pores having a mean pore diameter in range of about 10 µm to about 10000 µm, wherein the magnetic material is in the form of magnetic particles having a size in the range from about 1 nm to about 500 nm, and wherein porosity, pore size, pore connectivity, swelling agent concentration and/or specific volume of the composition undergoes a change from a first value to a second value, e.g., at least 10%, in response to an electromagnetic signal. It is to be understood that, change in one of porosity, pore size, pore connectivity, swelling agent concentration, and/or specific volume can be independent of change in one of the others, i.e., change in one may or may not effect a change in others.

The magnetic material-based compression compositions suitable for use in the methods of the present invention described herein can comprise any amount of matrix and magnetic materials. For example, the compositions can comprise 0.1-50% of the matrix material and 10-99% of the magnetic material. In some embodiments, the compositions comprise 1-25% of the matrix material and 75-99% of the magnetic material. Preferably, the compositions comprise 1-20% of the matrix material and 80-90% of the magnetic material. In some embodiments, the compositions comprise 1-15% of the matrix material and 85-99% of the magnetic material. In other embodiments, the compositions comprise 5-10% of the matrix material and 90-95% of the magnetic material. The percent values can be based on weight, volume and/or moles. In addition to the matrix and the magnetic materials, the composition suitable for use in the methods of the present invention can comprise additional substances such as a swelling agent. When an additional substance is present in the composition, matrix and magnetic material percent values are calculated based on the matrix and magnetic material only.

Alternatively, compositions suitable for use in the methods of the present invention can comprise 0.1%-50% of matrix material, 1-90% of magnetic material and a swelling agent in an amount corresponding to the balance up to 100%. Again percent values can be based on weight, volume and/or moles. In other embodiments, percent values are based on weight. In some embodiments, the composition comprises 0.1%-25% of matrix material, 5-50% of magnetic material and a swelling agent in an amount corresponding to the balance up to 100%. In some other embodiments, the composition comprises 0.1%-25% of matrix material, 10-50% of magnetic material and a swelling agent in an amount corresponding to the balance up to 100%. In some embodiments, the composition comprises 0.1%-10% of matrix material, 10-50% of magnetic material and a swelling agent in an amount corresponding to the balance up to 100%. In one embodiment, the composition comprises about 1% matrix, about 13% magnetic material and a swelling agent in an amount corresponding to the balance up to 100%.

Ratio of matrix to magnetic material in the composition can range from about 1:20 (matrix:magnetic) to about 20:1. The ratio can be in the range of from about 1:120 to about 10:1, from about 1:30 to about 5:1, or from about 1:20 to about 1:1. In some embodiments, the ratio is in the range of about 1:20 to about 1:5. In some embodiments, the ratio is around 1:13. In one preferred embodiment, the ratio is in the range from about 1:1 to about 3:1. It is to be understood that ratio can be based on weight, volume and/or moles.

In some embodiments, the composition suitable for use in the methods of the present invention is macroporous. As used herein, the term "macroporous" refers to the fact that composition comprises macropores. The composition suitable for use in the methods of the present invention can also comprise micropores. Generally, micropores are pores having a diameter on the order of about 50 Angstroms or less, while macropores are pores having a diameter on the order of about 100 Angstroms or greater. Generally, diameter of a pore is such as to allow free flow of swelling agent and/or a solvent through the pores. Pore diameters of compositions described herein can range from about 20 μm to 10000 μm. In some embodiments, the composition suitable for use in the methods of the present invention comprises pores having mean pore diameter in range from about 150 μm to 1000 μm, 200 μm to 1000 μm, 300 μm to 1000 μm, 400 μm to 1000 μm, 500 μm to 1000 μm, 600 μm to 1000 μm, 1000 μm to 10000 μm, 2000 μm to 10000 μm, 3000 μm to 10000 μm, 4000 μm to 10000 μm, 5000 μm to 10000 μm, or 6000 μm to 10000 μm. In some embodiments, the composition suitable for use in the methods of the present invention comprises pores having mean pore diameter in range from about 150 μm to 750 μm. In some embodiments, the composition comprises pores having mean pore diameter of 200-750 μm. In another embodiment, the composition comprises pores having mean pore diameter of 250-700 μm. In some embodiments, the composition comprises pores having mean pore diameter of 500-700 μm. In other embodiments, the composition comprises pores having mean pore diameter of 1000-7000 μm. In some embodiments, the composition comprises pores having mean pore diameter of 2000-7000 μm. In other embodiments, the composition comprises pores having mean pore diameter of 3000-7000 μm. In some embodiments, the composition comprises pores having mean pore diameter of 5000-7000 μm. In other embodiments, the composition comprises pores having mean pore diameter of about 100 μm, 200 μm, 300 μm, 400 μm, 500 μm, 600 μm, 700 μm, 800 μm, 900 μm, 1000 μm, 2000 μm, 3000 μm, 4000 μm, 5000 μm, 6000 μm, 7000 μm, 8000 μm, 9000 μm or 10000 μm.

The changes in porosity, pore size, pore connectivity, swelling agent concentration, and/or specific volume are preferably reversible (i.e., porosity, pore size, pore connectivity, swelling agent concentration, and/or specific volume detectably increases or decreases upon application of the stimuli, and then reverts to its original value, e.g., within 10%, 5%, 2%, 1% or less of the original value, when the stimuli is discontinued). However, it will be recognized that in some applications, reversibility of one or more of porosity, pore size, pore connectivity, swelling agent concentration, and/or specific volume is not essential. The change in specific volume is also referred to as a volume phase transition herein.

It is to be understood that external stimuli can be applied by providing a stimuli that is not present, by holding back a stimuli that is already present, or by changing the amount of a stimuli that is already present.

In some embodiments, in response to an electromagnetic signal, porosity, pore size, pore connectivity, swelling agent concentration, and/or specific volume changes by at least 10%, 15%, 20%, 25% 30%, 40%, 50%, 60%, 70%, 80%, 90%, 95%, 96%, 97%, 98%, 99% or more relative to the original value. In some embodiments, in response to an electromagnetic signal, porosity, pore size, pore connectivity, swelling agent concentration, and/or specific volume changes by at least 70% or more relative to the original value. In some embodiments, the porosity, pore size, pore connectivity, swelling agent concentration, and/or specific volume decreases in response to the electromagnetic signal. In other embodiments, the porosity, pore size, pore connectivity, swelling agent concentration, and/or specific volume increases in response to the electromagnetic signal.

As used herein, the term "porosity" means the fractional volume (dimension-less) of the composition that is composed of open space, e.g., pores or other openings. See for example, Coulson J. M., et. al., *Chemical Engineering* (1978), volume 2, 3rd Edition, Pergamon Press, 1978, page 126). In some embodiments, the composition has a porosity of 0.1 to 0.99. Generally, in the absence of an external electromagnetic signal, porosity of the composition can range from 0.5 to 0.99. Preferably porosity is in the range of from about 0.75 to about 0.99, more preferably from about 0.8 to about 0.95. Preferably, porosity of the porous material is at least 0.75, more preferably at least 0.8, and most preferably at least 0.9.

Several methods can be employed to measure porosity, including, direct methods (e.g. determining the bulk volume of the porous sample, and then determining the volume of the skeletal material with no pores (pore volume=total volume-material volume), optical methods (e.g., determining the area of the material versus the area of the pores visible under the microscope, where the areal and volumetric porosities are equal for porous media with random structure), imbibition methods (e.g., immersion of the porous sample, under vacuum, in a fluid that preferentially wets the pores), water saturation method (e.g., pore volume=total volume of water-volume of water left after soaking), water evaporation method (e.g., pore volume in cubic centimeters=weight of saturated sample in grams-weight of dried sample in grams), and gas expansion methods. Methods for measuring porosity of a sample are described in Glasbey, C. A. Horgan, G. W. and Darbyshire, J. F. *J Soil Sci* (1991) 42: 479-486, contents of which are herein incorporated by reference in their entirety.

In some embodiments, the composition suitable for use in the methods of the present invention is a particle, e.g., a nanoparticle or microparticle. The composition particle size will vary depending on the particular use intended for such a particle. In general, particles can have at least one dimension in the range from about 1000 μm to about 2000 μm, 1200 μm to about 2000 μm, 1300 μm to about 2000 μm, 1500 μm to about 2000 μm, 1600 μm to about 2000 μm, 1000 μm to about 1500 μm, 1100 μm to about 1500 μm, or 1200 to about 1500 μm.

Preparation of compositions suitable for use in the methods of the present invention described herein does not require a special type of matrix and/or magnetic materials. Any material that comprises a spatial network structure can be used for the matrix. The matrix can comprise materials of synthetic or natural origin (e.g., biopolymers) or a mixture thereof cross-linked by physical and/or chemical interactions. In some embodiments, the matrix is not biodegradable.

Some exemplary matrixes include swellable and non-swellable gels, elastomers, and rubbers. Swellable gels can include hydrogels and organogels. The term "hydrogel" indicates a cross-linked, water insoluble, water containing material. Hydrogels have many desirable properties for biomedical applications. For example, they can be made nontoxic and compatible with tissue, and they are usually highly permeable to water, ions and small molecules.

Gels generally comprise solid, cross-linked polymer networks capable of forming a stable system in equilibrium with an interpenetrating swelling agent. Many gel forming polymers are known in the art. Suitable gels include polymers, copolymers, and blockpolymers based on monomers containing ionizable groups or polymerizable double bonds. Exemplary monomers include, but are not limited to, acrylic acid, methyl methacrylate, methyl acrylic acid, ethyl acrylate, vinyl sulfonic acid, styrene, styrene sulfonic acid (e.g., p-styrene sulfonic acid), maleic acid, butenoic acid, vinyl phosphate, vinyl phosphonate, ethylene, propylene, styrene, vinyl methyl ether, vinyl acetate, vinyl alcohol, acrylonitrile, acrylamide, N—(C1-C6 alkyl) acrylamide (such as N-isopropylacrylamide, N-t-butylacrylamide), and the like. Gels are made by homopolymerizing or copolymerizing any of the foregoing monomers. Other suitable gel materials can include, alginate, chitosan, collagen, gelatin, hyaluronate, fibrin, agarose, and derivatives thereof. The gel can be a copolymer as described above into which has been incorporated as one comonomeric component a ligand that connects to, complexes or physically entraps the desired magnetic material.

The gel can be cross-linked to let it take a physically stable form when hydrated or dehydrated. Suitable cross-linking can be provided by incorporating about 0.5 wt. % to about 1.5% wt. % of a cross-linking agent into the gel. Cross-linking can also be provided by incorporating about 0.01 mol % to about 15 mol % of the cross-linking agent in the gel.

Suitable crosslinking agents include compounds whose molecule has a plurality of reactive groups. Such molecular crosslinking agents may be N,N'-methylene-bis acrylamide or divinylbenzene (DVB), ethylene glycol dimethacrylate, divinyl ketone, vinyl methacrylate and divinyl oxalate. Ionic crosslinkage which uses ions such as metallic ions may also be employed. Crosslinkage using electromagnetic waves such as gamma rays is also possible. Cross-linking can also be based on electrostatic interactions, hydrogen boding, hydrophobic interactions or (micro)crystal formation.

Ionically cross-linkable polymers can be anionic or cationic in nature and include but not limited to carboxylic, sulfate, hydroxyl and amine functionalized polymers. The cross-linking ions used to crosslink the polymers can be anions or cations depending on whether the polymer is anionically or cationically cross-linkable. Appropriate cross-linking ions include but not limited to cations selected from the group consisting of calcium, magnesium, barium, strontium, boron, beryllium, aluminum, iron, copper, cobalt, lead and silver ions. Anions can be selected from but not limited to the group consisting of phosphate, citrate, borate, succinate, maleate, adipate and oxalate ions. More broadly, the anions are derived from polybasic organic or inorganic acids. In some embodiments, the cross-linking cations are calcium, iron, and barium ions. In other embodiments, the cross-linking anion is phosphate. Cross-linking can be carried out by contacting the polymers with a nebulized droplet containing dissolved ions. One of ordinary skill in the art will be able to select appropriate cross-linking agent for the respective hydrogel used in the making of a multi-layer TE construct. For example, the gelation of collagen or alginate occurs in the presence of ionic cross-linker or divalent cations such as $Ca^{2+}$, $Ba^{2+}$ and $Sr^{2+}$.

In some embodiments, the gel comprises a biodegradable polymer selected from the group consisting of polyanhydrides, polyhydroxybutyric acid, polyorthoesters, polysiloxanes, polycaprolactone, poly(lactic-co-glycolic acid), poly(lactic acid), poly(glycolic acid), and copolymers prepared from the monomers of these polymers.

Suitable polymers which can be used in the composition suitable for use in the methods of the present invention include but are not limited to one or a mixture of polymers selected from the group consisting of polyurethanes, glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly glycolic acid (PGA), poly lactic-co-glycolic acid (PLGA), poly e-carpolactone (PCL), polyethylene oxide, poly propylene fumarate (PPF), poly acrylic acid (PAA), hydrolysed polyacrylonitrile, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch as well as salts and esters thereof. Polymers listed above which are not ionically cross-linkable are used in blends with polymers which are ionically cross-linkable.

Other preferred polymers include esters of alginic, pectinic or hyaluronic acid and C2 to C4 polyalkylene glycols, e.g. propylene glycol, as well as blends containing 1 to 99 wt % of alginic, pectinic or hyaluronic acid with 99 to 1 wt % polyacrylic acid, polymethacrylic acid or polyvinylalcohol. Preferred blends comprise alginic acid and polyvinylalcohol. Examples of mixtures include but are not limited to a blend of polyvinyl alcohol (PVA) and sodium alginate and propyleneglycol alginate.

In some embodiments, the gel is alginate, collagen, or agarose.

As used herein, the term "magnetic material" refers to a material or substance that is influenced by a magnetic field, i.e. relative permeability ($\mu r$) of the material is greater than unity. Such magnetic materials are intended to include those which are referred to as ferromagnetic, ferromagnetic, diamagnetic, paramagnetic, and superparamagnetic. As is the conventional understanding given that term, superparamagnetic materials exhibit magnetic properties only when in an externally applied magnetic field, and otherwise exhibit essentially no magnetic properties; and their total magnetism is greater than the sum of that of the individual particles considered separately. If the particle size of the magnetic material is sufficiently small, the magnetic material will most likely be superparamagnetic.

The magnetic properties of the composition are greatly influenced by the saturation magnetization, size, and concentration of magnetic material, as well as the strength of the external magnetic field.

The magnetic material can be any molecule, composition, particle, or substance, that exhibits magnetic properties when incorporated into the matrix. The magnetic materials can be selected from the group of elements having atomic numbers 21-29, 42, 44, and 57-70, elements having atomic numbers 24-29 or 62-69 being especially preferred. Preferably, a magnetic material is selected from the group including but not limited to, rare earth metals (such as gadolinium, terbium, dysprosium, holmium, erbium and europium), transient metals (such as iron, nickel, cobalt, magnesium chromium and copper), noble metals (such as rhodium, palladium), their oxides, compositions, combinations, solid dispersions, and alloys.

In some embodiments, the magnetic material is an iron oxide particle. In some embodiments, the magnetic material is selected from the group consisting of maghemite ($Fe_2O_3$), magnetite ($Fe_3O_4$), strontium ferrite, samarium-cobalt, neodymium-iron-boron (NIB), lodestone, pyrrhotite, $BaFe_{12}O_{19}$, Alnico magnet alloy, transfer salts of decamethylmetallocenes with 7,7,8,8-tetracyano-p-quinodimethane (TCNQ) or tetracyanoethylene (TCNE) (such as [Fe$(Cp^*)_2$]+[TCNE]−, [Fe$(Cp^*)_2$]+[TCNQ]−, [Cr$(Cp^*)_2$]+[TCNE]−, [Cr$(Cp^*)_2$]+[TCNQ]−, [Mn$(Cp^*)_2$]+[TCNE]−, and [Mn$(Cp^*)_2$]+[TCNQ]−), hexylammonium trichlorocuprate(II) ($CuCl_3(C_6H_{11}NH_3)$), Fe based amorphous magnetic powders, and combinations thereof. In some embodiments, the composition of the invention comprises two or more, e.g., two, three, four, or five, different magnetic materials.

Exemplary Fe based amorphous magnetic powders are described in U.S. Pat. App. Pub. No. 2009/0232693, the entire contents of which are incorporated herein by reference.

In some embodiments, magnetic material is a particle, e.g., a magnetic nanoparticle or magnetic microparticle. Depending on the size, porosity or pore size of matrix, magnetic particles can range in diameter from 1 nm to 1000 µm. Preferably magnetic particles are about 1 nm to 500 nm in diameter. In some embodiments, the magnetic particle is a magnetic nano-particle of diameter about 300 nm. Magnetic nanoparticles are a class of nanoparticle which can be manipulated using magnetic field. Such particles commonly consist of magnetic elements such as iron, nickel and cobalt and their chemical compounds. Magnetic nanoparticles are well known and methods described in the art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, the entire contents of all of which are incorporated herein by reference.

The magnetic material should be sufficiently immobilized in the matrix so that during any application of a magnetic field it cannot be removed therefrom by dissolution or chemical reaction that would be encountered, even as a result of a change in the porosity, pore size, pore connectivity, swelling agent concentration, and/or specific volume of the matrix. Thus, the magnetic material can be simply physically entrapped within the matrix, or it can be chemically bound into the matrix or complexed, encased in, or physically immobilized by an intermediate ligand which is in turn, chemically bound into the matrix. It is to be understood that physical immobilization includes chelation.

In some embodiments, the magnetic material is distributed homogeneously within the matrix material. In other embodiments, the magnetic material is distributed heterogeneously within the matrix material. The distribution of the magnetic material within the matrix material can be formed by application of a magnetic field during polymerization of the matrix material. In some embodiment, the magnetic material is distributed within the matrix material during polymerization of the matrix material in the presence of a uniform magnetic field. In other embodiments, the magnetic material is distributed within the matrix material during polymerization of the matrix material in the presence of non-uniform magnetic field. In some embodiments, the magnetic material is distributed into a separate compartment within the matrix material. In some embodiments, the magnetic material is distributed at one side within the matrix material distant from the electromagnetic signal.

Magnetic material-based compression compositions suitable for use in the methods of the present invention can be prepared using methods known in the art and easily adapted by one of skill in the art. For example, magnetic material can be bound to the matrix by carrying out the polymerization which forms the matrix in the presence of chelate-forming groups and then reacting this intermediate with an excess of the magnetic material in an aqueous solution. If desired, a bridging group, e.g., a linker, can be introduced between the chelate-forming groups and the matrix backbone.

Alternatively, the magnetic material can be present in cavities within the matrix, in the form of an insoluble or sparingly soluble substance or composition. The incorporation of the magnetic material within the matrix can be achieved in several ways.

In one method, dry or incompletely swollen matrix may be swelled in an appropriate solution comprising a salt of a metal, for instance chloride and/or sulfate of the metal, whereafter the matrix is dried. The matrix is then swelled again in a solution, of a substance which is capable of precipitating the metal in the form of an insoluble or sparingly soluble magnetic material, compound or complex. For instance the precipitating substance may be a soluble phosphate, such as sodium phosphate, when the phosphate of the metal is insoluble or sparingly soluble in the medium in which the matrix is swelled. Alternatively, the precipitating substance may be an alkali metal hydroxide when the hydroxide of the metal is insoluble or sparingly soluble in the medium in which the matrix is swelled.

As used herein, the term "magnetic metal" refers to any metal that exhibits magnetic properties when it is incorporated in the matrix. The magnetic metal may or may not exhibit magnetic properties while it is not incorporated in the matrix. As used herein, the term "magnetic metals" includes ions, salts, oxides or nitrides of the metal.

In another method, dry or incompletely swollen matrix material may be swelled in a solution comprising a solvent in which the matrix material swells, e.g., water or dimethylsulfoxide, and a magnetic material in a suitable chemical form and, optionally, one or more reagents. The one or more reagents, optionally in contact with the matrix, may produce a magnetic material in an elemental state or in an insoluble or sparing soluble state by a chemical reaction (which may involve the matrix), for example, a redox process, wherein the magnetic material is finely dispersed in the matrix.

According to another method, the matrix is prepared by a process involving a cross-linking reaction carried out in a medium in which magnetic material or a complex thereof is dispersed, the magnetic material or complex being insoluble or sparingly soluble in the medium. Thus, the magnetic material or complex will become entrapped in a dispersed form in cavities formed in the three-dimensional network of the matrix. Where the magnetic material is incorporated as a complex, this is preferably a chelate complex which is insoluble or sparingly soluble in aqueous media.

Methods for preparing ferrogels have been described, for example, in Sahiner, N. *Colloid Polym Sci* (2006) 285: 283; Sauzeddle, F. Elaissari, A. and Picho, C. *Colloid Polym Sci* (1999) 277: 846; Gu, S. Shiratori, T. and Konno, M. *Colloid Polym Sci* (2003) 281: 1076; Zhang, J. et al., *Adv Mater* (2002) 14: 1756; and Caykara, T. Yörök, D. and Demirci, S. *J App Polym Sci* (2009) 112: 800, the entire contents of all of which are incorporated herein by reference.

Once the matrix comprising magnetic material has been prepared, macropores can be introduced by freezing the matrix at a temperature ranging from about −10° C. to about −180° C. Pores can also be created by freezing the magnetic solution during the crosslinking reaction to create a cryogel. In some embodiments, the matrix is frozen at a temperature of about −15° C. to about −25° C. To prepare compositions comprising pores of a size of about 700 µm, a freezing temperature of about −20° C. is used. The lyophilized composition is then swelled in the appropriate swelling agent. Ferrogels frozen at about −20° C. with pores of a size of about 700 µm have a height of about 15 mm and a diameter of about 20 mm.

Compositions comprising different pore sizes can also be prepared. For example, compositions comprising pores of two different sizes for use in animal models can be prepared at a freezing temperature of about −20° C. At the freezing temperature of −20° C., two regions with different pore sizes can be produced in the same composition, wherein the regions rich in magnetic materials, e.g., iron oxide, have a pore size of about 340 µm, and the magnetic material-low regions have a pore size of about 140 µm. Ferrogels frozen at about −20° C. with two regions of different pore sizes, e.g., 340 µm and 140 µm, have a height of about 2 mm and a diameter of about 8 mm.

Similarly, this method of pore creation is suitable for generation of compositions comprising different pore sizes for use in humans, wherein the resulting pores in both magnetic material-rich and -low regions will have relatively larger pores when compared to the composition used in animal models. Generally, diameter of a pore is such as to allow free flow of swelling agent and/or a solvent through the pores. Typically, pore diameters of compositions described herein can range from about 20 µm to 10000 m. In some embodiments, the composition suitable for use in the methods of the present invention comprises pores having mean pore diameter in range from about 150 µm to 1000 µm, 200 µm to 1000 µm, 300 µm to 1000 µm, 400 µm to 1000 µm, 500 µm to 1000 µm, 600 µm to 1000 µm, 1000 µm to 10000 µm, 2000 µm to 10000 µm, 3000 µm to 10000 µm, 4000 µm to 10000 µm, 5000 µm to 10000 µm, or 6000 µm to 10000 µm. In some embodiments, the composition suitable for use in the methods of the present invention comprises pores having mean pore diameter in range from about 150 µm to 750 rm. In some embodiments, the composition comprises pores having mean pore diameter of 200-750 µm. In another embodiment, the composition comprises pores having mean pore diameter of 250-700 µm. In some embodiments, the composition comprises pores having mean pore diameter of 500-700 µm. In other embodiments, the composition comprises pores having mean pore diameter of 1000-7000 µm. In some embodiments, the composition comprises pores having mean pore diameter of 2000-7000 µm. In other embodiments, the composition comprises pores having mean pore diameter of 3000-7000 µm. In some embodiments, the composition comprises pores having mean pore diameter of 5000-7000 µm. In other embodiments, the composition comprises pores having mean pore diameter of about 100 µm, 200 µm, 300 µm, 400 µm, 500 µm, 600 µm, 700 µm, 800 µm, 900 µm, 1000 µm, 2000 µm, 3000 µm, 4000 µm, 5000 µm, 6000 µm, 7000 µm, 8000 µm, 9000 µm or 10000 µm.

Without wishing to be bound by theory, the choice of freezing temperature, device size and/or device shape affects porosity and pore size of the resultant composition.

In some embodiments, the composition of the invention has an elastic modulus in the range between $10^{-3}$ and $10^3$ kPa. As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The shear modulus or modulus of rigidity (G or µ) describes an object's tendency to shear (the deformation of shape at constant volume) when acted upon by opposing forces; it is defined as shear stress over shear strain. The shear modulus is part of the derivation of viscosity. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lamé's first parameter, and P-wave modulus.

In some embodiments, the compositions suitable for use in the methods of the present invention further comprise a compound to be delivered to the target tissue. The compound is selected from the group consisting of small organic or inorganic molecules; saccharines; oligosaccharides; polysaccharides; peptides; proteins; peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the composition may further include a bioactive agent. As used herein, "bioactive agents" or "bioactive materials" refer to naturally occurring biological materials, for example, extracellular matrix materials such as fibronectin, vitronection, and laminin; cytokines; growth factors; antibodies; vaccines and differentiation factors. "Bioactive agents" also refer to artificially synthesized materials, molecules or compounds that have a biological effect on a biological cell, tissue or organ.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, flt3-ligand, and tumor necrosis factor α (TNFα). Other examples are described in Dijke et al., *Bio/Technology*, 7:793-798 (1989); Mulder G D, Haberer P A, Jeter K F, eds. *Clinicians' Pocket Guide to Chronic Wound Repair*. 4th ed. Springhouse, Pa.: Springhouse Corporation; 1998:85; Ziegler T. R., Pierce, G. F., and Herndon, D. N., 1997, *International Symposium on Growth Factors and Wound Healing: Basic Science & Potential Clinical Applications* (Boston, 1995, Serono Symposia USA), Publisher: Springer Verlag.

In some embodiments, suitable bioactive agents include but are not limited to therapeutic agents. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents may be combined to the extent such combination is biologically compatible.

Exemplary therapeutic agents include, but are not limited to, those found in Harrison's Principles of Internal Medicine, 13th Edition, Eds. T. R. Harrison et al. McGraw-Hill N.Y., N.Y.; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the entire contents of all of which are incorporated herein by reference.

Examples of therapeutic agents which may be incorporated in the composition, include but are not limited to, narcotic analgesic drugs; corticosteroids; hormones; pharmaceuticals for arthritis treatment; antibiotics, including tetracyclines, penicillin, streptomycin and aureomycin; antihelmintic; canine distemper drugs applied to domestic animals and large cattle, for example, phenothiazine; antitumor drugs; anti-hypertensive drugs; anti-inflammatory agents; neuromuscular relaxants; anti-disrhythmic drugs; vasodilating drugs; anti-hypertensive diuretics; anticoagulants; hormones and peptides. It is understood that above list is not full and simply represents the wide diversification of therapeutic agents that may be included in the compositions. In some embodiments, the therapeutic agent is Mitoxantrone, protein (e.g. VEGF) or plasmid DNA.

The amount of therapeutic agent distributed in a composition depends on various factors including, for example, specific agent; function which it should carry out; required period of time for release of a the agent; quantity to be administered. Generally, dosage of a therapeutic agent i.e. amount of therapeutic agent in composition, is selected from the range about from 0.001% (w/w) up to 95% (w/w), preferably, from about 5% (w/w) to about 75% (w/w), and, most preferably, from about 10% (w/w) to about 60% (w/w).

In some embodiments, the composition comprises a cell, e.g. a biological cell. One way to incorporate cells into the composition is by re-swelling a dried or partially dried composition of the invention in an aqueous solution comprising the cells to be incorporated. The aqueous solution can comprise enough cells, such that from about $10^4$ to about $10^8$ cells/ml are deposited in the composition. In some embodiments, the aqueous solution comprises from about $10^4$ to about $10^6$ cells/ml. In one embodiment, the aqueous solution comprises about $5\times10^5$ cells/ml.

In some embodiments, the composition comprises more that one cell type. This can be accomplished by having two or more different cell types in aqueous solution used for swelling. When two or more different cell types are to be incorporated into the composition, total number of cells in the aqueous solution ranges from about $10^4$ to about $10^8$ cells/ml, about $10^4$ to about $10^6$ cells/ml, or about $10^5$ cells/ml.

Cells amenable to be incorporated into the composition include, but are not limited to, stem cells (embryonic stem cells, mesenchymal stem cells, bone-marrow derived stem cells and hematopoietic stem cells), chrondrocytcs progenitor cells, pancreatic progenitor cells, myoblasts, fibroblasts, keratinocytes, neuronal cells, glial cells, astrocytes, preadipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g., a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., 2007, *Science* 318: 1917-1920; Takahashi K. et. al., 2007, *Cell* 131: 1-12).

Cells useful for incorporation into the composition can come from any source, for example human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HUVEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stein cells (mESC) mouse neural precursor cells, mouse pancreatic progenitor cells mouse mesenchymal cells and mouse endodermal cells.

In some embodiments, tissue culture cell lines can be used in the compositions described herein. Examples of cell lines include but are not limited to C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and in "Cells for tissue engineering" by Heath C. A. (Trends in Biotechnology, 2000, 18:17-19) and the entire contents of all of which are incorporated herein by reference.

The bioactive agent can be covalently linked to the matrix through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

In some embodiments, the bioactive agent is bound to the matrix by a hydrolyzable bond. In some embodiments, the cell or the bioactive agent has a mean free path in the composition that is shorter than the mean free path of the cell or the bioactive agent in water.

A composition suitable for use in the methods of the present invention described herein can be administered to a subject by any appropriate route known in the art. As used herein, the term "administer" refers to the placement of a composition into or onto a subject by a method or route which results in at least partial localization of the composition at a desired site such that a desired effect is produced.

Exemplary modes of administration include, but are not limited to, injection, implantation, or topical application such as placing the compositions over the skin. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection. In some embodiments, the compositions are injected at the site of tissue damage. In other embodiments, the compositions are implanted at the site of injury upon major surgery to assist tissue regeneration or to treat tissue injury.

Compositions that are to be implanted can additionally include one or more additives. Additives may be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

For administration to a subject, composition comprising a bioactive agent can be formulated together with one or more pharmaceutically acceptable carriers (additives) and/or diluents. As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting a bioactive agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The composition suitable for use in the methods of the present invention can be of rectangular form from about 0.5 to about 50 cm in length and from about 0.1 to about 10 cm in width. For example, the composition may have a length from about 1 to about 10 cm, about 10 to about 50 cm, about 1 to about 20 cm, about 1 to about 30 cm, about 1 to about 40 cm, about 5 to about 20 cm, about 5 to about 30 cm, about 5 to about 40 cm, about 10 to about 30 cm, or about 10 to about 40 cm. The composition may have a width from about 0.1 to about 1 cm, 1 to about 10 cm, about 2 to about 10 cm, about 3 to about 10 cm, about 4 to about 10 cm, about 5 to about 10 cm, or about 6 to about 10 cm.

The composition suitable for use in the methods of the present invention can also be of cylindrical form from about 0.5 to about 30 cm in diameter and from about 0.1 to about 10 cm in length. For example, the composition may have a diameter from about 0.5 to about 1 cm, about 1 to about 10 cm, about 1 to about 20 cm, about 1 to about 30 cm, about 1 to about 5 cm, about 5 to about 10 cm, about 5 to about 20 cm, about 5 to about 30 cm, about 10 to about 30 cm, or about 20 to about 30. The composition may have a length from about 0.1 to about 1 cm, about 1 to about 10 cm, about 2 to about 10 cm, about 3 to about 10 cm, about 4 to about 10 cm, about 5 to about 10 cm, or about 6 to about 10 cm.

The composition suitable for use in the methods of the present invention can further be of circular shape with a diameter from about 0.5 to about 30 cm. For example, the composition may have a diameter from about 0.1 to about 10 cm, about 10 to about 30 cm, about 1 to about 20 cm, about 1 to about 30 cm, about 5 to about 10 cm, about 5 to about 20 cm, about 5 to about 30 cm, about 10 to about 20 cm, or about 20 to about 30 cm.

In some cases, the composition can be of a spherical shape. When the composition is in a spherical shape, its diameter can range from about 0.5 to about 10 cm. In some embodiments, the diameter of the composition is from about 1 to about 10 cm. In other embodiments, the diameter of the composition is from about 1 to about 5 cm. In some embodiments, the diameter of the composition is from about 5 to about 10 cm. In other embodiments, the diameter of the composition is from about 1 to about 3 cm. In some embodiments, the diameter of the composition is from about 3 to about 5 cm. In other embodiments, the diameter of the composition is from about 3 to about 10 cm.

B. Controller-Based Compression Devices

A controller-based compression device suitable for use in the methods of the present invention comprises a surrounding member configured to encircle a body part including a site of tissue damage and apply cyclic mechanical compressions to the tissue, and a controller configured to generate the cyclic mechanical compressions in the surrounding member.

In some embodiments, the surrounding member includes a sleeve that encircles a body part that includes the site of tissue damage. In some embodiments, the compression device is configured to externally encircle a body part or at least a portion of a body part that includes the site of tissue damage. In some embodiments, the compression device is configured to be disposed at least partially internally within the body and at least partially encircle the body that includes the site of tissue damage.

In some embodiments, a controller associated with the surrounding member is used to generate the cyclic mechanical compressions in the surrounding member. As used herein, a "controller" is a device or system configured to generate cyclic mechanical compressions and to control properties of the cyclic mechanical compressions, such as, the frequency, the amplitude and/or the duration of the cyclic mechanical compressions being generated. In some embodiments, the controller includes a microcontroller that controls the properties of the cyclic mechanical compressions. In some embodiments, the controller includes storage for holding machine readable instructions, measurements of pressure from a pressure sensor, or other information. In some embodiments, microcontroller includes storage for holding machine readable instructions, measurements of pressure from a pressure sensor, or other information. In some embodiments, the controller includes additional storage that is not included in the microcontroller, but is accessible to the microcontroller for holding machine readable instructions, measurements of pressure from a pressure sensor, or other information.

In some embodiments, the controller is included in the compression device. For example, the controller and the surrounding member may be included in a single unit in the compression device. In some embodiments, the compression device includes the controller and the surrounding member and is configured to be worn. In some embodiments, a compression device suitable for use in the methods of the present invention described herein is suitable for wearable applications. In some embodiments, the compression device is wearable and untethered such that the wearer can be mobile during the cyclic mechanical compressions. In some embodiments, the controller is separate from the compression device. In some embodiments, the controller is separate from, but coupleable with one or more components of a compression device (e.g., coupleable with a surrounding member of the compression device). In some embodiments, the controller is portable.

In some embodiments, the compression device is electromagnetically actuated, pneumatically actuated or hydraulically actuated to apply the cyclic mechanical compressions to the tissue. In some embodiments, the controller includes a pump. In some embodiments, the pump is a pneumatic air pump. In some embodiments the controller includes a microcontroller that provides instructions to the pump.

In some embodiments, the surrounding member includes one or more inflatable portions (e.g., one or more inflatable chambers, one or more inflatable bladders, one or more inflatable members, or a combination of the aforementioned). In some embodiments, a surrounding member of the compression device comprises at least 2, 3, 4, 5, 6, 7, 8, 9, or 10 inflatable portions. In some embodiments, the one or more inflatable portions are configured to be inflated with a gas, e.g., air. In other embodiments, the one or more inflatable portions are configured to be inflated with a liquid, e.g., water. In some embodiments, the one or more inflatable portions are configured to be inflated by an electromagnetic signal. In some embodiments, the one or more inflatable portions are configured to be independently inflated and deflated. In some embodiments, only some of the one or more inflatable portions are configured to be independently inflated and deflated.

In some embodiments, at least partial inflation of at least some of the one or more inflatable portions is used to apply the cyclic mechanical compressions to the tissue. In some embodiments, increasing a pressure of inflation of at least some of the one or more inflatable portions is used to apply the cyclic mechanical compressions to the tissue. In some embodiments, at least some of the one or more inflatable portions aid in contacting the tissue with the compression device (e.g., to aid in fitting the surrounding member to the body part). In some embodiments, some of the one or more inflatable portions aid in contacting the tissue with the compression device and others of the inflatable portions are used to apply the cyclic mechanical compressions to the tissue. For example, some inflatable portions are used to maintain a constant low level of inflation to maintain a fit of the surrounding member around a body part while one or more other inflatable portions disposed over the site of tissue damage are cyclically inflated and deflated.

In some embodiments, at least some of the one or more inflatable portions are parts of a unitary structure (e.g., different inflatable portions of a unitary sleeve that may be independently inflatable). In some embodiments, at least some of the one or more inflatable portions are separate inflatable members that are not portions of a unitary structure (e.g., a balloon or bladder disposed within a pocket of a sleeve that includes inflatable sections).

Inflation of some or all of the inflatable portions of the surrounding member may occur sequentially or simultaneously, or in part sequentially and in part simultaneously, to generate cyclic mechanic compression at a target site, e.g., the site of tissue damage, thereby promoting tissue regeneration and/or repair at the site of tissue damage. Inflation of at least some of the one or more inflatable portions can be regulated by the controller of the compression device. For example, the controller (e.g., a microcontroller system) can be programmed to control one or more valves associated individually, groupwise, or collectively, with the one or more inflatable portions. For example, each inflatable portion may have an associated valve to control flow, one valve may control a flow into a group of inflatable portions while another valve may control flow into another group of inflatable portions, or one valve may control flow into all the inflatable portions. Using the one or more valves, the one or more inflatable portions can be inflated, or the inflation pressure increased, for a pre-determined time (e.g., 500 ms), followed by a period of time (e.g., 500 ms) of deflation, when no pressure is applied or when a decreased pressure is applied. Such a cycle of inflation, or increased inflation pressure, and deflation may be applied at a pre-determined frequency, e.g., 1 Hertz. In some embodiments, the controller includes storage holding readable instructions for applying the inflation pressure to at least some of the one or more inflatable portions of the surrounding member to generate the cyclic mechanical compressions in the surrounding member.

The particular time periods for inflation and deflation can vary depending on the conditions of the subjects and/or the purpose of the methods. In some embodiments, the inflatable portions can be inflated, or the inflation pressure increased, for at least 5 seconds, followed by a deflation period of 5 seconds. In other embodiments, the inflatable portions can be inflated, or the inflation pressure increased, for at least 10 seconds, followed by a deflation period of at least 10 seconds. In some embodiments, the inflatable portions can be inflated, or the inflation pressure increased, for at least 15 seconds, followed by a deflation period of at least 15 seconds. In other embodiments, the inflatable portions can be inflated, or the inflation pressure increased, for at least 20 seconds, followed by a deflation period of at least 20 seconds. In some embodiments, the inflatable portions can be inflated, or the inflation pressure increased, for at least 30 seconds, followed by a deflation period of at least 30 seconds. In other embodiments, the inflatable portions can be inflated, or the inflation pressure increased, for at least 60 seconds, followed by a deflation period of at least 60 seconds.

In some embodiments, the inflatable portions can be inflated, or the inflation pressure increased, for at least 1 minute every 1, 2, 3, 4, 5, 6, 7, 8, 9 or 10 hours. In other embodiments, the inflatable portions can be inflated, or the inflation pressure increased, for at least 2 minutes every 1, 2, 3, 4, 5, 6, 7, 8, 9 or 10 hours. In some embodiments, the inflatable portions can be inflated, or the inflation pressure increased, for at least 5 minutes every 1, 2, 3, 4, 5, 6, 7, 8, 9 or 10 hours. In other embodiments, the inflatable portions can be inflated, or the inflation pressure increased, for at least 10 minutes every 1, 2, 3, 4, 5, 6, 7, 8, 9 or 10 hours. In some embodiments, the inflatable portions can be inflated, or the inflation pressure increased, for at least 15 minutes every 1, 2, 3, 4, 5, 6, 7, 8, 9 or 10 hours. In other embodiments, the inflatable portions can be inflated, or the inflation pressure increased, for at least 20 minutes every 1, 2, 3, 4, 5, 6, 7, 8, 9 or 10 hours.

In some embodiments, the inflatable portions can be inflated, or the inflation pressure increased, for at least 1 minute every 12 hours. In other embodiments, the inflatable portions can be inflated, or the inflation pressure increased, for at least 2 minutes every 12 hours. In some embodiments, the inflatable portions can be inflated, or the inflation pressure increased, for at least 5 minutes every 12 hours. In other embodiments, the inflatable portions can be inflated, or the inflation pressure increased, for at least 10 minutes every 12 hours. In some embodiments, the inflatable portions can be inflated, or the inflation pressure increased, for at least 15 minutes every 12 hours. In other embodiments, the inflatable portions can be inflated, or the inflation pressure increased, for at least 20 minutes every 12 hours.

The frequency for applying mechanical compressions can also vary from subject to subject, or from condition to condition. In some embodiments, the inflatable portions can be inflated, or the inflation pressure increased, with a frequency from at least a 1 Hz to 500 Hz. In some embodiments, the inflatable portions can be inflated, or the inflation pressure increased, with at least a 1 Hz frequency. In other embodiments, the inflatable portions can be inflated, or the inflation pressure increased, with at least a 2 Hz frequency. In some embodiments, the inflatable portions can be inflated, or the inflation pressure increased, with at least a 3 Hz frequency. In other embodiments, the inflatable portions can be inflated, or the inflation pressure increased, with at least a 4 Hz frequency. In some embodiments, the inflatable portions can be inflated, or the inflation pressure increased, with at least a 5 Hz frequency. In other embodiments, the inflatable portions can be inflated, or the inflation pressure increased, with at least a 6 Hz frequency. In some embodiments, the inflatable portions can be inflated, or the inflation pressure increased, with at least a 7 Hz frequency. In other embodiments, the inflatable portions can be inflated, or the inflation pressure increased, with at least a 8 Hz frequency. In some embodiments, the inflatable portions can be inflated, or the inflation pressure increased, with at least a 9 Hz frequency. In other embodiments, the inflatable portions can be inflated, or the inflation pressure increased, with a frequency of at least 10 Hz, 15 Hz, 20 Hz, 30 Hz, 40 Hz, 50 Hz, 60 Hz, 70 Hz, 80 Hz, 90 Hz, 100 Hz, 200 Hz, 300 Hz, 400 Hz or 500 Hz.

Accordingly, the capability to regulate the frequency as well as the duration of inflation of the inflatable portions allows the level of cyclic mechanical compression to be varied from subject to subject. For example, a subject with superficial disease may be treated effectively by a low level of compression whereas a subject with a severe condition may need a higher level of compression. In some embodiments, the compression devices are configured to exert a peak pressure of about 1 kPa at the site of tissue damage. In other embodiments, the compression devices are configured to exert a peak pressure of about 2 kPa. In some embodiments, the compression devices are configured to exert a peak pressure of about 3 kPa. In other embodiments, the compression devices are configured to exert a peak pressure of about 4 kPa. In certain embodiments, the compression devices are configured to exert a peak pressure of about 5 kPa. Thus, actuation of the compression devices results in cyclic mechanical compressions at the site of tissue damage, thereby promoting tissue regeneration and/or repair at the site of tissue damage. It is possible to provide the pressure profile needed to treat these various indications through the use of a compression device as described herein.

The controller may further comprise at least one pressure sensor (e.g., air pressure sensor, or surface pressure sensors that can be resistive or capacitance measures) attached to the surrounding member and disposed within the surrounding member (e.g., internally within a sleeve of the surrounding member) or disposed between a force exerting portion of the surrounding member and a body part (e.g., on an inward facing surface of a sleeve configured to be positioned between an inflatable portion that exerts compressive pressure on the site of tissue damage and the body part of the subject). The pressure sensor provides readings of the pressure experienced by the site of tissue damage, e.g., the limb, due to the inflation of one or more inflatable portions of the surrounding member by the controller. These sensors may be based on conductive fabrics or elastomers and can enable monitoring of applied pressure to signals delivered to the one or more inflatable portions of the surrounding member. The controller may also comprise an accelerometer or other soft strain and pressure sensors that can measure the frequency and amplitude of the vibration or cyclic mechanical compressions at one or more inflatable portions in the surrounding member.

Monitoring the actual pressure experienced by a site of tissue damage, e.g., a limb of a subject, due to the compression device, enables the compression device to provide a pre-determined compression profile to the site of tissue damage, e.g., the limb. The pre-determined compression pressure profile may be selected by a heath case professional based on the subject's condition.

In some embodiments, the sensor also allows the compression device to regulate, e.g., increase or decrease, pressure at a specific location of a body part when desired to do so. In some embodiments, for a compression device including multiple inflatable portions the controller may be programmed to inflate only selected portions of the compression device. For example, where there is a site of tissue damage at a specific part of a limb of a subject, not all the inflatable portions need be inflated to apply cyclic mechanical compressions, and only those specific ones overlying the site of tissue damage will be inflated.

In some embodiments, for a compression device including multiple inflatable portions (e.g., multiple independently inflatable chambers), the compression device includes a plurality of sensors with each sensor associated with a corresponding inflatable portion to monitor the pressure experienced at a site of tissue damage, e.g., a limb of a subject, due to pressure from that inflatable portion. In some embodiments, with a plurality of independently inflatable portions (e.g., independently inflatable chambers), a sensor is associated with each independently inflatable portion to monitor the pressure experienced at a site of tissue damage due to pressure from that independently inflatable portion. This enables the compression device to precisely control the pressure in each inflatable portion to achieve the desired pressure profile. In some embodiments, the controller includes storage storing machine readable instructions for applying an inflation pressure to one or more inflatable portions of a surrounding member to generate the cyclic mechanical compressions in the surrounding member, receiving information regarding a pressure measurement from a pressure sensor associated with one of the inflatable portions, and modifying one or both of a level of the inflation pressure applied or a time period that the inflation pressure is applied to the one or more inflatable portions based on the information regarding a pressure measurement received from the pressure sensor.

In some embodiments, due to the sensors and monitoring capacity of the compression device and the microcontroller system present in the controller, it is possible to monitor the usage of the compression device by a subject. In some embodiments, the controller includes storage configured to store information a from a pressure sensor regarding a plurality of pressure measurements acquired during application of cyclic mechanical compressions to tissue of the subject. For example, the controller may store information regarding the actual pressures applied against the subject's tissue during cyclic compressions to aid in confirming that the device has been used properly. Knowledge of the extent of usage will enable a heath care professional to prescribe the most suitable treatment for the next stage of healing or prevention.

In some embodiments, a surrounding member of a compression device includes one or more soft actuators, which are used to apply cyclic mechanical compressions to the tissue. As used herein, the term "soft actuator" refers to an actuator consisting of elastomeric matrices with embedded flexible materials (e.g., cloth, paper, fiber, particles). Soft actuators for use in the compression devices include any actuators known in the art. Exemplary actuators include, but not limited to, a fiber reinforced actuator, a Pneunet bending actuator, a McKibben actuator, a pleated air muscle, a balloon, an inflatable, a motor, a vibrating motor, a cable, an electroactive material, e.g., a shape memory alloy, an electrostatic or a dielectric elastomer, and combinations thereof. The controller can control actuation of the soft actuators through the control of fluid (i.e., liquid or gas) flow into and out of the soft actuators. The controller can also control actuation of the soft actuators by applying an electromagnetic signal.

Soft actuators suitable for use in the compression devices of the present invention can be designed and fabricated using any methods and materials that are known in the art and easily adapted by one of skill in the art. These actuators can be rapidly fabricated in a multi-step molding process and can achieve combinations of pre-designed motions, such contraction, extension, bending and twisting with simple control inputs such as pressurized fluid or air. See, e.g., U.S. Pat. Nos. 6,718,766, 6,772,673, US2014/0109560A1, WO2013/130760A2, WO2015/157560A1 and WO2015/061444A1. The entire contents of each of the foregoing applications are incorporated herein by reference.

In some embodiments, a surrounding member includes at least 1, 2, 3, 4, 5, 6, 7, 8, 9, or 10 soft actuators. In some embodiments, an inflatable portion of a surrounding member includes a channel in which the soft actuator is disposed. In some embodiment, the actuators are integrated into the surrounding member in discrete parts. In other embodiments, the actuators are integrated together as part of the manufacturing process.

In some embodiments, a surrounding member includes a matrix material that encircles or surrounds a body part that includes the site of tissue damage. Matrix materials for use in the compression devices include, but are not limited to: a textile, a fabric, a mesh, a silicone elastomer, a rubber, and combinations of the aforementioned.

In some embodiments, a surrounding member of a compression device includes a balloon (e.g., an urethane balloon in a sleeve including the matrix material). In some embodiments, the balloon is disposed within a pocket of the matrix material (e.g., in a pocket of a sleeve). In other embodiments, a balloon is disposed over the subject's skin at the site of tissue damage and the matrix material (e.g., a sleeve) is disposed encircling the balloon and the body part (e.g., a part of a limb) that is the site of tissue damage. The compression device applies cyclic mechanical compressions to the damaged tissue through the skin, thus promoting regeneration and/or repair of the damaged tissue.

In some embodiments, the balloon of the compression device can be of a spherical shape. When the balloon is in a spherical shape, its diameter can range from about 0.5 to about 10 cm; about 1 to about 10 cm; about 1 to about 5 cm; about 5 to about 10 cm; about 1 to about 3 cm; about 3 to about 5 cm or about 3 to about 10 cm.

The size and/or a shape of the surrounding member may be determined based on the size, shape or structure of the body part that includes the site of the tissue damage. For example, the size and shape of a surrounding member for tissue damage in a knee may be different than the size and shape of a surrounding member for tissue damage in a shoulder, in a finger, or in an abdomen. Further, the size and/or shape of the surrounding member may be determined, at least in part, by the size and shape of an area of tissue damage in the body part. In some embodiments, the compression device includes one surrounding member. In some embodiments, the compression device includes multiple surrounding members.

In some embodiments, the surrounding members (e.g., sleeves) of the compression devices suitable for use in the methods of the present invention described herein are customizable for different geometries and morphologies. The surrounding member may be adjustable or configurable for encircling different sizes and/or different types of body parts. In some embodiments, the surrounding members can wrap around the site of the tissue damage (e.g., the limb) adopting the shape of the limb. In other embodiments, a surrounding member has a shape similar to the anatomical features of a body part of a subject (e.g., a leg, a foot, an arm, a wrist, a neck, a shoulder, a knee or a joint) enabling the surrounding member to fit comfortably onto the body part of the subject. Compression devices can be configured to surround any desired location (e.g., a site of tissue damage) of a subject in need thereof for application of cyclic mechanical compressions at the target location to promote regeneration and/or repair of the damaged tissue in the subject.

In some embodiments, the surrounding members of the compression devices are light weight and low profile, which enables a subject to use the compression devices wearing ordinary clothes and shoes. In some embodiments, a compression device suitable for use in the methods of the present invention described herein is suitable for wearable applications. In some embodiments, the compression device is configured to apply the cyclic mechanical compressions to the tissue while being worn and being physically untethered to any other medical equipment. In some embodiments, the compression device is self-contained and configured to be worn. Accordingly, in some embodiments, the compression devices suitable for use in the methods of the invention are convenient to operate and are suitable for normal routine life style.

Unlike the existing commercially available wearable (e.g., self-contained and untethered) devices, which primarily focus on the use of passive compression, in some embodiments, compression devices suitable for use in the methods of the present invention are able to generate active mechanical compressions while being worn and untethered. By incorporating soft actuators or inflatable portions and controllers into the wearable compression devices of some embodiments, active and programmable cyclic mechanical compressions can be generated, which promote regeneration and/or repair of tissue at the site of tissue damage and improve the healing potential of the damaged tissue.

One of ordinary skill in the art will appreciate that some of the methods described herein can also be performed using compression devices and compression systems that are tethered (e.g., where not all components of the compression device or compression system is wearable) or that are not self-contained.

In some embodiments, the surrounding members of the compression devices that are configured to surround a site of tissue injury are oblong in shape (e.g., rectangular, oval, elliptical, or irregular in shape with one dimension longer than the other) from about 0.5 to about 50 cm in length and from about 0.1 to about 10 cm in width. For example, the surrounding members of the compression device may have a length from about 1 to about 10 cm, about 10 to about 50 cm, about 1 to about 20 cm, about 1 to about 30 cm, about 1 to about 40 cm, about 5 to about 20 cm, about 5 to about 30 cm, about 5 to about 40 cm, about 10 to about 30 cm, or about 10 to about 40 cm. The surrounding members of the compression device may have a width from about 0.1 to about 1 cm, 1 to about 10 cm, about 2 to about 10 cm, about 3 to about 10 cm, about 4 to about 10 cm, about 5 to about 10 cm, or about 6 to about 10 cm.

In some embodiments, the surrounding members of the compression devices that are configured to surround at a site of injury are, at least in part, cylindrical in shape with the cylindrical portion being about 0.5 to about 30 cm in diameter and from about 0.1 to about 10 cm in length. For example, a surrounding member of a compression device may have a cylindrical portion with a diameter of about 0.5 to about 1 cm, about 1 to about 10 cm, about 1 to about 20 cm, about 1 to about 30 cm, about 1 to about 5 cm, about 5 to about 10 cm, about 5 to about 20 cm, about 5 to about 30 cm, about 10 to about 30 cm, or about 20 to about 30. The cylindrical portion may have a length from about 0.1 to about 1 cm, about 1 to about 10 cm, about 2 to about 10 cm, about 3 to about 10 cm, about 4 to about 10 cm, about 5 to about 10 cm, or about 6 to about 10 cm.

A composition suitable for use in the methods of the present invention described herein can be administered to a subject by any appropriate route known in the art. Exemplary modes of administration include, but are not limited to, implantation, or topical application such as placing the composition over the skin. In some embodiments, the compression device is configured to be disposed externally to the body and surrounds at least a portion of a body part that is the site of tissue damage (e.g., a limb, a spine, a neck, a waist, a shoulder, a knee, a joint, an ankle, a calf, a thigh, a foot, a hand, a wrist, an arm, a shoulder, or an axilla). For example, the compression devices are wrapped around the site of tissue damage or placed over the site of tissue damage to apply cyclic mechanical compressions over the target site. In some embodiments, the compression device is configured to be implanted, or disposed, at least partially, internally within the body and to, at least partially, surround a body part that includes the site of tissue damage. In some embodiments, the surrounding member of the compression device is implanted at the site of tissue damage at least partially encircling or surrounding an esophagus of a subject. In other embodiments, the surrounding member of the compression device is implanted at the site of tissue damage encircling or surrounding an urethral or anal sphincter of a subject. In some embodiments, the compression devices are implanted at the site of tissue damage upon major surgery to assist tissue regeneration or to treat tissue damage.

Compositions that are to be implanted can additionally include one or more additives. Additives may be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

FIG. 8 schematically depicts components of a compression device 100 in accordance with some embodiments of the invention. The compression device 100 includes a surrounding member 110 configured to encircle a body part including a site of tissue damage and apply cyclic mechanical compressions to the tissue at the site of tissue damage and a controller 120 configured to generate the cyclic mechanical compressions in the surrounding member. The surrounding member 110 includes an inflatable portion in the form of a balloon 112. The controller 120 includes a microcontroller 122 configured to control one or more of the following: a frequency of compression cycles, a total duration of compression cycles, a length of a period of increasing compression in a single cycle, a length of a period of decreasing compression in a single cycle, or a peak compression level. The controller 120 also includes a pump 124 configured to provide fluid in the form of a liquid or a gas to the inflatable portion (e.g., balloon 112). The controller 120 also includes a valve 126 configured to control fluid flow between the pump 124 and the inflatable portion (e.g., balloon 112). Operation of the valve 126 is controlled by the microcontroller 122.

In some embodiments, the compositions suitable for use in the methods of the present invention described herein are free of any biologics as described herein, e.g., a bioactive agent, or a cell. Application of mechanical stimulation alone, i.e., cyclic mechanical compressions, to the target tissue is sufficient to enhance functional tissue regeneration and to reduce fibrosis and inflammation at the injured tissue. Accordingly, the biologic-free composition may offer a simple yet effective alternative to cell-based or drug-based therapies when treating tissue injuries.

In some embodiments, the compositions suitable for use in the methods of the present invention are combined with existing biologic-based therapies to treat tissue injury. For example, incorporation of cyclic mechanical compressions into existing drug and cell delivery systems, that employ both mechanical and biological interventions, could potentially lead to a new combinatorial therapies that generate enhanced regenerative outcomes.

The present invention is further illustrated by the following examples, which are not intended to be limiting in any way. The entire contents of all references, patents and published patent applications cited throughout this application, as well as the Figures, are hereby incorporated herein by reference.

Examples

The following methods were used in the examples below unless otherwise specified.
Materials and Methods
Materials Medical grade, high molecular weight (~250 kDa) sodium alginate with high guluronate content (Protanal LF 20/40) was purchased from FMC Biopolymers (Oslo, Norway). Alginates were used following covalent RGD modification and dialysis purification, as previously described (Rowley et al., (1999) *Biomaterials* 20(1): 45-53). All other chemicals including adipic acid dihydrazide (AAD), 1-ethyl-3-(dimethylaminopropyl) carbodiimide (EDC), MES, 1-hydroxybenzotriazole (HOBT), Iron(II,III) oxide powder (<5 μm, 310069) were purchased from Sigma-Aldrich (St. Louis, Mo.).
Animals and Surgical Procedures All animal work was performed in compliance with NIH and institutional guidelines. Six-week-old female wild-type C57BL/6J mice (Jackson Laboratories, Bar Harbor, Me., USA) were anesthetized with an intraperitoneal injection of ketamine (80 mg kg$^{-1}$) and xylazine (5 mg kg$^{-1}$). For myotoxin injuries, the tibialis anterior muscles of the right legs of anesthetized mice were injected with 10 μl of 10 μg/ml Notexin Np myotoxin from Notechis Scutatus snake venom (Latoxan) using a 25 μl Hamilton syringe. Six days after notexin injection, hindlimb ischemia was induced by unilateral external iliac and femoral artery and vein ligation, as previously described (Silva E A & Mooney D J (2007) *J. Thromb. Haemost.* 5(3):590-598; Chen R R, et al. (2007) *FASEB J.* 21(14):3896-3903). After vessel ligation, a hydrated ferrogel scaffold was placed subcutaneously on the tibialis anterior muscle in certain conditions and the incision was surgically closed.
Ischemia and Perfusion Analysis Blood perfusion measurements of the ischemic and normal limb were performed on anesthetized animals (n=10) using a Laser Doppler Perfusion Imaging (LDPI) analyzer (PeriScan PIM II, Perimed Instruments, Ardmore, Pa.). Entire hindlimbs were scanned under basal conditions and then every other day following surgery. Perfusion was calculated as the ratio of ischemic to non-ischemic limb perfusion for each animal.
Ferrogel Scaffold Stimulation Biphasic ferrogels (7 wt % iron oxide) were fabricated with alginate covalently modified with RGD peptide (DS 10, 10 RGD peptides per alginate chain), as previously described (Cezar C A, et al. (2014) *Adv. Healthcare Mater.* 3, 1869-1876). While non-degradable alginate was used to simplify the system, oxidized alginate can be used in the future to create ferrogels with controlled degradation. In this case, optimization of iron oxide nanoparticle size, shape, and surface charge may be necessary to ensure particle absorption by the lymphatic capillary system and clearance from the body. Prior to implantation, biphasic ferrogel scaffolds were hydrated with 100 μL PBS. Biphasic ferrogel scaffolds were then placed subcutaneously on the tibialis anterior muscle and stimulated for 5 min at 1 Hz every 12 hours by approaching and retracting a permanent magnet with a surface field of 6510 Gauss (K&J Magnetics, DXOZO). The ferrogel implant and magnet were orientated so that magnetic stimulation resulted in compression of the ferrogel against the injured muscle. Following retrieval at 3 days and 2 weeks, scaffolds were fixed in 10% neutral-buffered neutral buffered formalin overnight. Ferrogels were then paraffin embedded, sectioned at 7 μm thickness, and stained with hematoxylin and eosin at the Harvard Rodent Histopathology Core. For pressure profile generation, an Instron 3342 single column apparatus (10 N load cell) configured for tensile testing was used. A custom adapter that allowed for stimulation of the ferrogel far from the load cell was attached to the top tensile grip, and the ferrogel was cyclically stimulated with a permanent magnet.

Pressure Cuff Stimulation

For mechanical stimulation using the balloon pressure cuff, a spherical low durometer urethane balloon (10-15 mm diameter 10000000FA, Vention medical) was attached to flexible silicone tubing (1.78 mm outer diameter, 1.1 mm inner diameter, McMaster Carr) and bonded at each neck with UV cure adhesive (Loctite 3943, Henkel). The output from two solenoid valves (TE miniature switching solenoid valves, sensor technics) was joined and connected to the balloon. Valve inlets were connected to a pneumatic air pump (pneumatic pump M0019057, Parker electronics) at the pressure and vacuum outlets respectively. The valves were wired to 2-channel relay board with two SRD-05 VDC-SL-C relays that were controlled by an Arduino Uno microcontroller developer board. The microcontroller was programmed to sequentially open the valves for 500 ms every second so that the balloon would be pressurized for 500 ms and then evacuated for 500 ms at a 1 Hz frequency. The balloon was placed inside a polycarbonate cylindrical cuff made from a 20 ml syringe body trimmed to length with the plunger removed (20 mm outer diameter, 40 mm length, adjustable wall thickness from 2-4 mm using polycarbonate cylindrical liners). For pressure cuff stimulation, the mouse leg was placed in the cuff and the balloon was fixed directly above the tibialis anterior muscle outside the skin. The balloon was then inflated and deflated for 5 min at 1 Hz every 12 h. For pressure profile generation, an Instron 3342 single column apparatus (10 N load cell) configured for compression testing was used. The balloon was removed from the cylindrical cuff and cyclically inflated and deflated between two stationary compression platens separated by a distance equal to the diameter of the deflated balloon.

Histologic Assessment of Skeletal Muscle

Mice were sacrificed and hindlimb muscle tissues (n=10) were processed for histologic analyses. Tibialis anterior muscles were fixed in 10% neutral buffered formalin overnight, paraffin embedded, and sectioned at 7 μm thickness. Sections stained with H&E were used for quantification of mean fiber diameter, inflammatory infiltrate, and fibers with centrally located nuclei. All histologic analyses performed on H&E stained sections were performed in a blinded fashion. M1 macrophages were identified with immunostaining for mouse CCR7 (Abcam ab32527; Invitrogen A-11035). Vascular endothelial cells were identified by immunostaining for mouse CD31 (Abcam ab28364; Invitrogen A-11035). Interstitial fibrosis was assessed in picosirius stained sections imaged with polarized light. Quantification of CCR7 and CD31 immunostaining was performed using ImageJ.

Muscle Function Testing

Intact tibialis anterior muscles were dissected (n=5/condition), mounted vertically midway between two cylindrical parallel steel wire electrodes (1.6 mm diameter, 21 mm long) attached by their tendons to microclips connected to a force transducer (FORT 25, WPII) and bathed in a physiologic saline solution in a chamber with continuously bubbled oxygen at 37° C. Muscle length was adjusted to a physiological relevant length. A wave pulse was initiated using a custom-written LabVIEW program and delivered to the stimulation electrodes via a purpose-built power amplifier (QSC USA 1310). Contractions were evoked every 5 min. Tetani was evoked at 250-300 Hz and 25-30 V, with a constant pulse width of 2 ms and a train duration of 1 s. Peak tetanic force was determined as the difference between the maximum force during contraction and the baseline level. Forces were then normalized to muscle wet weight.

Oxygen Probe

An OxyLab pO2 instrument and implantable optical probe (Oxford Optronix, Oxford, UK) were used to measure rapid temporal changes in intramuscular dissolved oxygen and temperature during biphasic ferrogel stimulation. Briefly, the probe was inserted using a 16 g needle catheter, and the tip was carefully placed in the midbelly region of the tibialis anterior muscle. A biphasic ferrogel was then implanted subcutaneously above the muscle containing the probe as before (Cezar C A, et al. (2014) *Adv. Healthcare Mater.* 3, 1869-1876), and the incision was closed around the probe. Oxygen and temperature readings were recorded continuously before, during, and after biphasic ferrogel stimulation at 1 second intervals.

Statistical Analyses

All statistical comparisons were performed using ANOVA with Bonferroni's post-hoc test and a two-tailed unpaired Student's t-test with Welch's correction and analyzed using INSTAT 3.1a (GraphPad Software, Inc., San Diego, Calif., USA) software. Differences between conditions were considered significant if $p<0.05$.

Example 1. Experimental Design and Muscle Stimulation Profiles

The tibialis anterior muscle of each C57BL6/J mouse was subjected to a severe dual injury involving an intramuscular injection of notexin followed by induction of hindlimb ischemia six days later, as previously described (Borselli C et al., (2011) *Biomaterials* 32(34):8905-8914). Complete loss of locomotion of the injured hindlimb was observed immediately following induction of ischemia. Following ischemic surgery, the injured muscle was treated with a subcutaneously implanted biphasic ferrogel, subsequently stimulated at 1 Hz for 5 min every 12 hrs noninvasively using a permanent magnet (FIG. 1A). Control conditions included a pressure cuff stimulated at 1 Hz for 5 min every 12 hours, a biphasic ferrogel without stimulation, magnetic field only, and no treatment. The biphasic ferrogel provides stimulation directly to the muscle. The pressure cuff externally compresses the muscle through the skin. Both stimulation of the biphasic ferrogel and the pressure cuff led to uniform cyclic compressions on the injured muscle. Importantly, biphasic ferrogels exhibited fatigue resistance as Young's modulus and toughness changed minimally throughout the 2 week study (FIGS. 7A and 7B). Stimulated biphasic ferrogels were able to exert a peak pressure of 1.2 kPa while the pressure cuff was able to exert a slightly larger peak pressure of 2.0 kPa. The kinetics of the compressions varied between the biphasic ferrogel and the pressure cuff, with the biphasic ferrogels exhibiting more gradual changes in pressure while the pressure cuff demonstrated more rapid changes in pressure (FIGS. 1B and 1C).

Example 2. Host Response to Ferrogel Implant

Biphasic ferrogels were histologically examined 3 days and 2 weeks following implantation in order to determine the host response to the implants. Upon retrieval, all scaffolds were found localized at the initial site of implantation. Initial orientation of the gel relative to the skin and injured muscle tissue remained unchanged throughout the study. Additionally, no significant differences in gel thickness were observed between stimulated and non-stimulated ferrogels. At 3 days, both stimulated and non-stimulated biphasic ferrogels remained largely acellular and no fibrous capsule was seen surrounding the implants. At 2 weeks, a fibrous capsule surrounding all biphasic ferrogel implants was observed (FIG. 2A). Non-stimulated biphasic ferrogels were surrounded with a capsule of ~120 µm thickness while stimulated biphasic ferrogels were surrounded with a significantly thinner capsule of ~75 µm thickness (FIG. 2B).

Example 3. Markers of Muscle Regeneration: Centrally Located Nuclei and Muscle Fiber Size In order to determine the histological quality of muscle regeneration, several markers of muscle regeneration were examined. Areas of active muscle regeneration were present in all treatment conditions as indicated by muscle fibers containing centrally located nuclei (Hawke T J & Garry D J (2001) *J Appl Physiol* (1985) 91(2):534-551). Although no statistically significant differences were observed at 2 weeks, greater than 40% of fibers contained centrally located nuclei in all conditions except the no treatment control (30%) (FIGS. 3A and 3B). Mean muscle fiber size, as measured by cross-sectional area, remained fairly constant (~100 µm$^2$) in all tested conditions 3 days post-injury, as expected. However, at 2 weeks, mean muscle fiber size was generally greater in muscles treated with stimulated biphasic ferrogels (205 µm$^2$) when compared to no treatment controls (130 µm$^2$) (FIGS. 3A and 3C). Interestingly, a significant increase in mean muscle fiber size from 3 days to 2 weeks was only seen in muscles treated with stimulated biphasic ferrogels.

Example 4. Inflammation: Interstitial Fibrosis, Inflammatory Infiltrate, and Macrophage Presence The influence of cyclic mechanical compressions on inflammation and fibrosis was next examined using histologic sections. The extent of muscle fibrosis was assessed by visualizing picosirius red stained collagen I and III under polarized light. Interestingly, at 2 weeks, stimulated biphasic ferrogels showed significantly less interstitial fibrosis when compared to no treatment controls (FIGS. 4B and 4E). In contrast, all other treatment conditions remained statistically equivalent at this time point. In addition, quantification of the inflammatory infiltrate followed a similar trend. Unlike all other conditions, a significantly lower number of muscle infiltrating inflammatory cells were observed in stimulated biphasic ferrogel conditions when compared to no treatment controls (FIGS. 4A and 4D). Finally, stimulation of injured muscles by biphasic ferrogels and pressure cuff controls significantly reduced M1 macrophage infiltration, as measured by CCR7 staining (FIGS. 4C and 4F).

Example 5. Angiogenesis, Hindlimb Perfusion, and Oxygen

The ability of cyclic mechanical compressions to promote hindlimb reperfusion and angiogenesis was examined next. Induction of hindlimb ischemia led to a dramatic decrease in perfusion relative to the contralateral control limb, from 100% to ~30% immediately following surgery in all treatment groups (FIG. 5A), as expected. At 3 days, perfusion increased to ~40% in all conditions. A difference between the stimulated and non-stimulated biphasic ferrogel conditions appeared at day 9, but did not persist to day 14. A significant increase in perfusion of the muscle tissue was observed upon treatment of the pressure cuff (FIG. 5D). Differences in the average capillary density in muscle sections between the various conditions, as measured by immunostaining for the endothelial cell marker CD31, were not observed (FIG. 5B). The oxygen concentration within the muscle remained at a fairly constant baseline level of ~20 mmHg before biphasic ferrogel stimulation (FIG. 5C). Upon stimulation, however, intramuscular oxygen concentration rapidly increased and remained elevated until stimulation ceased. Upon cessation of ferrogel stimulation, the oxygen concentration rapidly returned to the previous baseline levels.

Example 6. Muscle Function: Contraction Force

To assess the functional quality of muscle regeneration, the contractile force of each injured and contralateral control muscle was measured. At 2 weeks, injured muscles treated with stimulated biphasic ferrogels and pressure cuffs showed significant increases in specific peak tetanic force, 2.6 and 2.2 fold over no treatment controls, respectively (FIG. 6). Stimulated biphasic ferrogels also showed a significant increase in specific peak tetanic force over the magnetic field only control (1.9 fold). In contrast, no significant difference in specific peak tetanic force was observed between the no treatment, magnetic field only, and non-stimulated biphasic ferrogel conditions.

To understand whether cyclic compressive stimulation improves muscle regeneration in a temporal manner, pressure-cuff mediated mechanical stimulation was applied on the injured taibialis anterior muscle for different durations (3, 7, and 14 days) at 1 Hz for 5 minutes every 12 hours with a peak pressure of 2.0 kPa. As shown in FIG. 9, the contractile force of injured muscle was progressively enhanced during the 14-day course of treatments. The average contractile force of the muscle treated with mechanical stimulation for 14 days was significantly higher than their control counterpart (no stimulation).

Example 7. Effect of Cyclic Mechanical Compression on Cytokine Levels

The effect of cyclic mechanical compressions on modulating the levels of cytokines in injured tissue was examined next. Briefly, 113 cytokines were screened from lysates of the tibialis anterior muscle treated with and without mechanical stimulation for 7 days after ischemic injury. As shown in FIG. 10, around 70 out of 113 cytokines were found to have a lower level of expression (top) in the muscle treated with mechanical stimulation by varying degrees as compared to their control counterparts (from 1.1 to 2.7 times). In addition, the molecules most significantly decreased in the muscle treated with mechanical compressions are closely associated with pro-inflammatory responses such as myeloperoxidase, neutrophil gelatinase-associated lipocalin, interleukin-17A and interleukin-6. Only a few cytokines were detected to have a higher level of expression (bottom) in the muscle tissue treated with mechanical compressions (up to 1.2 times). These data indicate that mechanical compressions indeed can modulate the levels of cytokines in injured tissue.

Subsequently, the effect of cyclic mechanical compression on intramuscular convection was assessed. Briefly, fluorescently labeled dextran (40 kDa) was injected into the tibialis anterior muscle and the change in fluorescent intensity of the injected dextran was monitored before and after mechanical compression by In Vivo Imaging Instruments. As shown in FIG. 11, the fluorescent intensity of the dextran significantly increased in the muscle treated with mechanical stimulation relative to their control group (no stimulation). This might be because cyclic compression caused a change in intramuscular convection, for example, by expelling the intramuscularly injected dextran out of the muscle toward the skin, and consequently the signals from molecules close to the skin might contribute to the enhanced fluorescent intensities.

Overall, these findings indicate that cyclic mechanical compressions can modulate the levels of various cytokines in the injured muscle tissue, which can potentially influence the regenerative processes of injured muscle. Moreover, this change in the cytokine levels might be due to the altered intramuscular convection by cyclic compression.

DISCUSSION

The present invention demonstrated that direct mechanical stimulation can enhance the regeneration of severely damaged skeletal muscle, obviating the need for exogenous growth factors or cells. These studies were carried out using a murine model of severe muscle injury involving both myotoxin-induced direct muscle damage and hind limb ischemia. This model leads to substantial necrosis of the muscle, fibrosis and loss of significant contractile function (Borselli C et al., (2011) *Biomaterials* 32(34):8905-8914), mimicking severe injuries in humans.

Actuation of biologic-free ferrogels resulted in mechanical compressions that affected the host inflammatory response towards the gel and led to a reduction in fibrous capsule thickness following 2 weeks of implantation. Strikingly, mechanical stimulation led to a significant reduction in fibrosis and inflammation of the injured muscle, demonstrating a potential immunomodulatory role for ferrogel-driven cyclic compressions. As assessed histologically, severe muscle injury resulting from myotoxin injection and hindlimb ischemia led to subsequent active muscle regeneration that was enhanced by stimulated biphasic ferrogels. In addition, mechanical stimulation led to a temporary increase in oxygen concentration at the site of injury. Biologic-free ferrogel and pressure cuff driven mechanical compressions led to enhanced muscle regeneration and muscle function when compared to no treatment controls, demonstrating the therapeutic potential of these mechanical interventions.

Actuation of both the biphasic ferrogel and the pressure cuff results in uniform cyclic compressions of the severely injured muscle tissue. The pressure cuff was roughly tuned so that the peak pressure values achieved by each system were comparable. The peak pressure value achieved by the pressure cuff remained slightly larger than that achieved by the biphasic ferrogel, and the kinetics of the pressure profiles also varied. Both the biphasic ferrogel and pressure cuff systems were able to apply a force (normalized to tibialis anterior wet weight) of ~2 N/g, a value similar to that used previously for massage-like compressive loading of rabbit tibialis anterior muscles injured with eccentric exercise (Haas C, et al. (2013) *Br. J. Sports Med.* 47(2):83-88). Stimulation parameters may be chosen to yield mechanical compressions that approximate those achieved with massage. In addition, the frequency, amplitude, and duration of the stimulations may be optimized for the tissue injury being addressed.

Biphasic ferrogel stimulation leads to a reduction in fibrous capsule thickness and inflammatory cells present in the surrounding muscle following 2 weeks of implantation, and this may relate to expulsion of inflammatory cells due to cyclic compression of the ferrogels. It is possible that invading cells near the scaffold edges were expelled from the ferrogel system upon stimulation, due to fluid convection resulting from large gel deformations, leading to an overall diminished cell presence within the scaffold. The decrease in M1 macrophage presence with ferrogel stimulation further suggests a potent immunomodulatory role for cyclic mechanical compressions. Taken together, these studies provide evidence that cyclic compressions, e.g., ferrogel-driven cyclic compressions and pressure cuff-driven compressions, may be useful to alleviate inflammation in certain tissue, e.g., muscle injuries. Further, this ability to inhibit fibrous capsule formation with cyclic compressions has potential utility for implantable drug delivery devices and sensors that require unobstructed diffusion around the implant for proper function.

Severe muscle injury resulting from myotoxin injection and hindlimb ischemia leads to active muscle regeneration that can be enhanced with stimulated biphasic ferrogels. While centrally located nuclei were observed in all conditions, significant increases in the mean muscle fiber size of regenerating fibers over time were only observed in muscles treated with stimulated biphasic ferrogels. Past reports suggest increased mean fiber diameter is indicative of tissues that have progressed further in the regenerative process (Borselli C, et al. (2010) *Proc. Natl. Acad. Sci. U.S.A.* 107(8):3287-3292; Wang L, et al. (2014) *Mol. Ther.* 22(8), 1441-1449).

Mean muscle fiber size values remained remarkably consistent among all treatment groups at this time point. At 2 weeks, pressure cuff controls exhibited a smaller mean fiber size than stimulated ferrogels suggesting that the ferrogel-driven cyclic mechanical compressions provide an additional, likely convection-based benefit. Specifically, enhanced fluid transportation around the implant site may accelerate immune cell and/or metabolic waste product removal. Interestingly, ferrogel-driven mechanical stimulation produces a therapeutic effect on muscle fiber size of the same order of magnitude as that achieved by previous approaches that delivered cells and drugs to severely injured muscle (Borselli C, et al. (2010) *Proc. Natl. Acad. Sci. U.S.A.* 107(8):3287-3292; Wang L, et al. (2014) *Mol. Ther.* 22(8), 1441-1449).

Cyclic mechanical compressions do not lead to an enhancement in hindlimb reperfusion and angiogenesis, but may instead lead to temporary increases in convection through the tissue or blood flow to the injured limb. While small differences in perfusion were present 9 days post-injury, they did not persist to the end of the study, suggesting that growth factor or cell support may be required to maintain any increases in perfusion that appear due to cyclic mechanical compressions alone. Strikingly, although steady-state hindlimb perfusion and capillary density were not significantly affected, oxygen probe experiments demonstrated an increase in oxygen concentration during the time in which biphasic ferrogel-driven cyclic mechanical compressions were being generated in the muscle. Likely, enhanced intramuscular convection driven by tissue compressions may have led to increased oxygen levels and expedited removal of metabolic byproducts that inhibit regeneration. Alternatively, cyclic compressions may increase oxygen concentration by locally and temporarily increasing blood flow to the injured muscle. Strikingly, biphasic ferrogel and pressure cuff driven cyclic mechanical compressions of injured muscle led to significant functional muscle regeneration. Following 2 weeks of treatment, biphasic ferrogel and pressure cuff treatment conditions showed 2.6- and 2.2-fold increases in peak tetanic force over no treatment conditions, respectively. While additional biomaterial-based approaches have induced similar improvements in muscle function through the co-delivery of myogenic bioagents with endothelial cells to enhance vascularization (5.5 fold increase in active stress over blank scaffold) or neural stem cells to promote innervation of muscle constructs (2.0 fold increase in maximum tetanic force over nerve-deficient control) (Koffler J, et al. (2011) *Proc. Natl. Acad. Sci. U.S.A.* 108(36):14789-14794; Shandalov Y, et al. (2014) *Proc. Natl. Acad. Sci. U.S.A.* 111(16):6010-6015; Morimoto Yi et al., (2013) *Biomaterials* 34(37):9413-9419; Larkin L M, et al., (2006) *In Vitro Cell. Dev. Biol. Anim.* 42(3-4):75-82; Rowley J A et al, (1999) *Biomaterials* 20(1): 45-53; Chen R R, et al. (2007) *FASEB J.* 21(14):3896-3903), no bioagents were delivered from the scaffolds in this study. The current study is the first report of functional muscle regeneration due to cyclic mechanical compressions in a severe model of muscle damage.

Strikingly, the results of these studies indicate a ferrogel scaffold and pressure cuff can be used to mechanically stimulate and regenerate severely injured muscle tissue without the use of growth factors or cells. The demonstration of functional muscle regeneration with a biologic-free material system may offer a simple yet effective alternative to cell-based therapies when treating certain types of muscle injuries. Further, incorporation of cyclic mechanical compressions into existing drug and cell delivery systems could potentially lead to a new combinatorial therapies that generate enhanced regenerative outcomes. While this study focuses on the repair of skeletal muscle, bioagent-free devices, such as ferrogels and pressure cuffs, and the concept of mechanically driven regeneration are expected to find broad utility and can likely be applied to other tissues and diseases.

EQUIVALENTS

Those skilled in the art will recognize, or be able to ascertain using no more than routine experimentation, many equivalents to the specific embodiments of the invention described herein. such equivalents are intended to be encompassed by the following claims.

We claim:
1. A method for promoting regeneration of a tissue in a subject in need thereof, comprising:
contacting the tissue with a composition comprising a matrix material and a magnetic material distributed therethrough, wherein the composition comprises macropores having a mean pore diameter in the range of about 10 μm to about 10000 μm, wherein the magnetic material is in the form of magnetic particles having a size in the range from about 1 nm to about 500 nm, and wherein porosity, pore size, pore connectivity, and/or specific volume of the composition changes by at least 10% in response to an electromagnetic signal; and
applying cyclic mechanical compressions to the tissue, thereby promoting regeneration of the tissue,
wherein the composition is free of a bioactive agent, a therapeutic agent, a cell, or a combination thereof.

2. The method of claim 1, wherein the cyclic mechanical compressions are caused by the electromagnetic signal, or by pneumatic or hydraulic actuation.

3. The method of claim 1, wherein the composition comprises a swelling agent, wherein the swelling agent concentration changes by at least 10% in response to an electromagnetic signal.

4. The method of claim 1, wherein the composition has a porosity of 0.1 to 0.99.

5. The method of claim 1, wherein the matrix material is a polymer, a cross-linked polymer, a copolymer, or a block polymer gel.

6. The method of claim 1, wherein the matrix material comprises a polymer selected from the group consisting of polyurethanes, glycosaminoglycan, silk, fibrin, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.

7. The method of claim 1, wherein the magnetic material is ferromagnetic, ferrimagnetic, diamagnetic, paramagnetic, or superparamagnetic material.

8. The method of claim 1, wherein the macropores have a mean pore diameter in the range of about 150 μm to about 7500 μm.

9. The method of claim 1, wherein porosity, pore size, pore connectivity, swelling agent concentration, and/or specific volume changes by at least 25% in response to the electromagnetic signal.

10. The method of claim 1, wherein the magnetic material is distributed homogeneously within the matrix material.

11. The method of claim 1, wherein the magnetic material is distributed heterogeneously within the matrix material.

12. The method of claim 11, wherein the heterogeneous distribution of the magnetic material within the matrix material is formed by application of a magnetic field during polymerization of the matrix material.

13. The method of claim 11, wherein the magnetic material is distributed into a separate compartment within the matrix material or is distributed at one side within the matrix material distant from the electromagnetic signal.

14. The method of claim 1, wherein the composition is suitable for implantation within the tissue.

15. The method of claim 1, wherein the tissue is damaged and the cyclic mechanical compressions are applied to the site of tissue damage (i) within less than 5, 10, 20, 30, 40, 50, 60 minutes after the damage has occurred; (ii) at least 1, 2, 3, 4, 5, 6, 7, 8, 9, 10, 12, or 24 hours after the damage has occurred; (iii) at least 1, 2, 3, 4, 5, 6, 7, 8, 9, 10 days or at least 1, 2, 3, 4, 5, 6, 7, 8, 9, 10 11, 12, 24, 48 or 60 months after the damage has occurred; (iv) over a period of at least 1, 2, 3, 4, 5, 6, 7, 8, 9, 10, 11, 12, 24, 36, 48, 60, 72, 84, 96 or 120 hours; (v) over a period of at least 14 days; or (vi) for about 1 to 30 days, about 1 to 50 days, about 1 to 100 days, about 1 to 200 days or about 1 to 300 days.

\* \* \* \* \*